(12) United States Patent
Molnar et al.

(10) Patent No.: US 9,658,060 B2
(45) Date of Patent: *May 23, 2017

(54) LIGHT FIELD IMAGE SENSOR, METHOD AND APPLICATIONS

(71) Applicant: CORNELL UNIVERSITY, Ithaca, NY (US)

(72) Inventors: Alyosha Molnar, Ithaca, NY (US); Albert Wang, Ithaca, NY (US); Patrick Gill, Sunnyvale, CA (US)

(73) Assignee: CORNELL UNIVERSITY, Ithaca, NY (US)

( * ) Notice: Subject to any disclaimer, the term of this patent is extended or adjusted under 35 U.S.C. 154(b) by 194 days.

This patent is subject to a terminal disclaimer.

(21) Appl. No.: 14/462,039

(22) Filed: Aug. 18, 2014

(65) Prior Publication Data
US 2015/0125943 A1 May 7, 2015

Related U.S. Application Data

(63) Continuation of application No. 13/282,806, filed on Oct. 27, 2011, now Pat. No. 8,809,758, which is a continuation-in-part of application No. 13/055,566, filed as application No. PCT/US2009/051660 on Jul. 24, 2009, now Pat. No. 8,530,811.

(60) Provisional application No. 61/083,688, filed on Jul. 25, 2008, provisional application No. 61/407,202, filed on Oct. 27, 2010.

(51) Int. Cl.
*H01L 27/00* (2006.01)
*G01B 11/14* (2006.01)
*G01S 3/782* (2006.01)
*H01L 27/144* (2006.01)
*G01N 21/64* (2006.01)

(52) U.S. Cl.
CPC ............. *G01B 11/14* (2013.01); *G01N 21/64* (2013.01); *G01S 3/782* (2013.01); *H01L 27/1446* (2013.01); *G01N 2201/062* (2013.01)

(58) Field of Classification Search
CPC ...................... G02B 27/4205; H01L 27/14625
USPC .......................................... 250/208.1, 237 G
See application file for complete search history.

(56) References Cited

U.S. PATENT DOCUMENTS

| 8,809,758 B2* | 8/2014 | Molnar | G02B 27/4205 250/208.1 |
| 2012/0267515 A1* | 10/2012 | Wu | G02B 21/0044 250/214 P |

* cited by examiner

*Primary Examiner* — Thanh Luu
(74) *Attorney, Agent, or Firm* — Bond, Schoeneck & King, PLLC; William Greener

(57) ABSTRACT

An angle-sensitive pixel (ASP) device that uses the Talbot effect to detect the local intensity and incident angle of light includes a phase grating disposed above a photodiode assembly or a phase grating disposed above an analyzer grating that is disposed above a photodiode assembly. When illuminated by a plane wave, the upper grating generates a self-image at a selected Talbot depth. Several such structures, tuned to different incident angles, are sufficient to extract local incident angle and intensity. Arrays of such structures are sufficient to localize light sources in three dimensions without any additional optics.

11 Claims, 33 Drawing Sheets

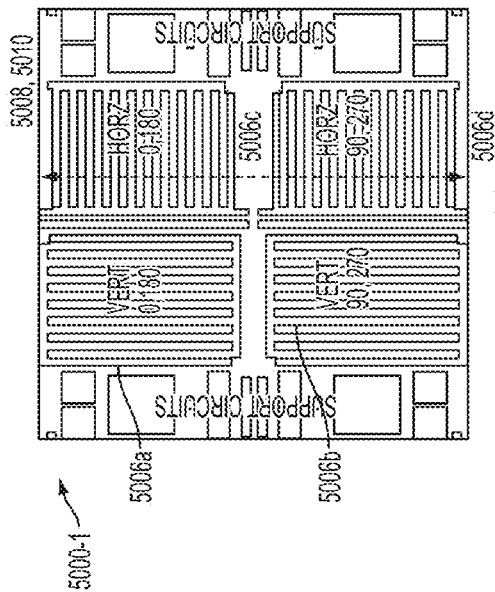
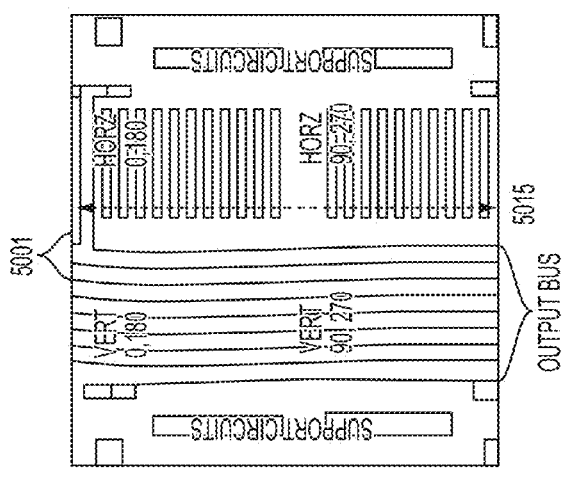
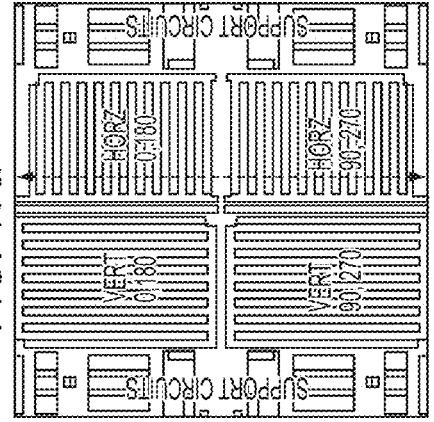

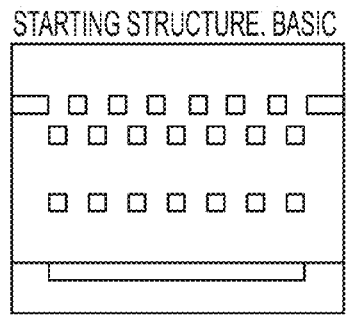
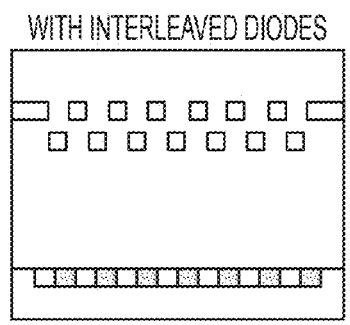
FIG. 27a
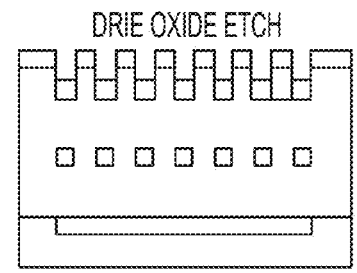
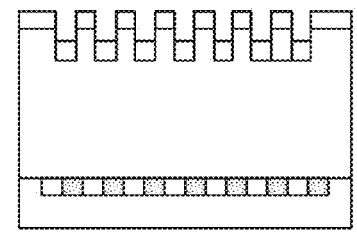
FIG. 27b
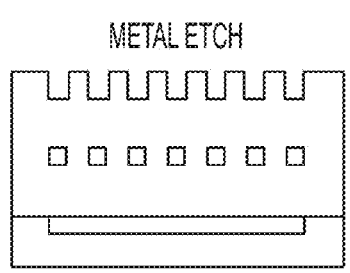
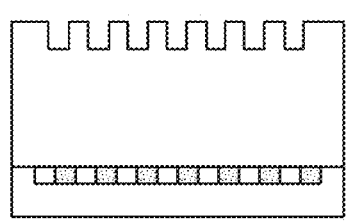
FIG. 27c
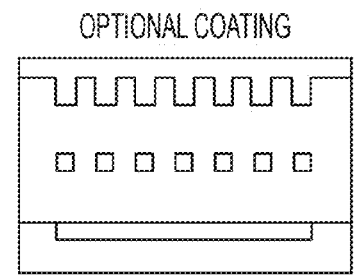
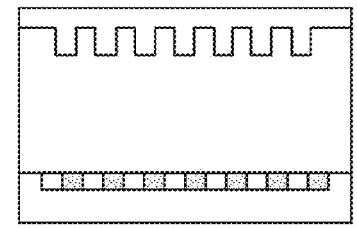
FIG. 27d

US 9,658,060 B2

LIGHT FIELD IMAGE SENSOR, METHOD AND APPLICATIONS

RELATED APPLICATION DATA

The instant application is a continuation (CON) of U.S. application Ser. No. 13/282,806, filed Oct. 27, 2011 and claims priority thereto as well as to U.S. application Ser. No. 13/055,566 filed on Apr. 6, 2011, which is a US National Stage filing of PCT/US09/51660 filed on Jul. 24, 2009, which claims priority to U.S. Provisional application Ser. No. 61/083,688 filed on Jul. 25, 2008, and further claims priority to U.S. Provisional application Ser. No. 61/407,202 filed on Oct. 27, 2010, the subject matters of which are incorporated herein by reference in their entireties.

FEDERALLY SPONSORED RESEARCH

This invention was made with Government support under Grant Number 5R21EB009841-01 awarded by the National Institute of Health. The United States Government has certain rights in the invention.

BACKGROUND

1. Field of the Invention

Embodiments of the invention are generally directed to the field of light field sensing and light field image detection. More particularly, embodiments of the invention are directed to a lens-less, angle-sensitive pixel (ASP) sensor and ASP devices having increased quantum efficiency and pixel density, which can measure the intensity and incident angle of a light field to provide an image of the light field. Embodiments of the invention further include, without limitation, imaging methods associated with said sensor and device embodiments, and applications thereof.

2. Related Art Discussion

Conventional imaging uses a large array of light sensors to create a map of light intensity at an image plane. However, this intensity map fails to capture incident angle, polarization angle, and other properties of light rays passing through the image plane. A complete description of these additional parameters defines the light field or, "flow" of light, at the image plane.

Michael Faraday first proposed the concept of light as a field in the mid 1800's. This concept was expanded by the theory of a "light field" in three-dimensional space. At a given point, the light field is defined by the infinite collection of vectors that represent the light arriving at the point from all angles. The light field can be formally defined by a "plenoptic function" of multiple variables. The plenoptic function parameterizes the light rays passing through all space in terms of intensity, I, which is dependent on position in space (x, y, z), direction ($\theta$, $\phi$), wavelength ($\lambda$), time (t), and polarization angle (p). Hence, $I(x, y, z, \theta, \phi, \lambda, t, p)$ is the complete representation of a visual scene and contains all possible views of the scene.

Measuring the plenoptic function would require an observer to be able to determine the intensity of every ray, for every wavelength, at all instants in time and at every point in space. Clearly, perfect determination of the plenoptic function for any practical scene is impossible. However, a number of techniques collectively known as light-field imaging have been devised that can record aspects of the plenoptic function beyond simple intensity at a plane. One reported method is to use an array of pinhole cameras, where each camera captures the incident angle-dependent intensity $I(\theta, \phi)$ at a particular location, $(x_0, y_0)$. Cameras at different positions $(x_i, y_i)$ capture a slice of the plenoptic function, $I(x, y, \theta, \phi)$. Arrays of conventional cameras can also be used, as can camera scanning, or multiple masks. Small-scale solutions have used microlenses to emulate camera arrays. However, all of these approaches require a significant number of parallel or moveable optical components to capture information about the light field beyond a simple intensity map.

Recording information about the light field of a scene provides a more complete description of that scene than a conventional photograph or movie, and is useful for a number of applications. The light field allows prediction of illumination patterns on a surface given known sources and the three-dimensional reconstruction of scenes (e.g., "light-field rendering" or "three-dimensional shape approximation"). FIGS. 1a, 1b show how one aspect of the light field, e.g., incident angle, can be used to localize a light source in three-dimensional space. Capturing the light field also permits construction of images with an arbitrary focal plane and aperture. This capability is useful in both photography and in microscopy for obtaining multiple focal planes without moving optics.

A wide variety of applications require information about the three-dimensional structure of microscale samples. Direct capture of this information using commodity semiconductor chips with no additional hardware would reduce the size and cost of many instruments and assays by orders of magnitude. Existing solid-state image sensors employ large arrays of photosensitive pixels that capture an intensity map of incident light, but no angle information. In typical imaging applications, a lens is required to ensure that the intensity map represents some object of interest. Without a lens, one must rely purely on the information contained in the light rays striking the image sensor. If a sample is placed sufficiently close to the image sensor and illuminated, the resulting intensity map will typically contain some blurred two-dimensional spatial information. Three-dimensional information is completely lost. Information contained in the incident angle of light rays is of interest because it contains further recoverable spatial information.

To date, macroscopic angle-detectors have been demonstrated in unmodified integrated circuit technology. Pixel-scale angle-sensitive structures have been demonstrated on chip but require post-assembled arrays of microlenses, which significantly increase cost and complexity over the manufacture and use of standard imagers.

Another reported technique involves silicon-on-insulator (SOI) structures utilizing regions of metal that are large relative to the wavelength of the light to generate a shadow on an underlying photodiode. This approach has been reportedly used to perform a single angle measurement but is not well suited to deployment in imager arrays.

The inventors recognize that solutions and improvements to the shortcomings and challenges in the prior art are necessary and would be beneficial. More specifically, in contrast to other approaches that require multiple lenses and/or moving parts, devices that are monolithic, require no optical components aside from the sensor itself, and which can be manufactured in a standard planar microfabrication process (e.g., CMOS) would be advantageous in the art. The embodiments of the invention disclosed and claimed herein successfully address these matters and achieve these goals.

The inventors further recognize that the metallic structures used to form the micron-scale fine-pitch transmission amplitude gratings to create the interference patterns from the incident light field, of the instant invention, block a significant fraction of the available light. While reduced light sensitivity is not a significant problem for many applications, maintaining high sensitivity comparable to that of a traditional photodetector permits more widespread deployment of angle-sensitive imagers. In addition, the combination of this 'top' grating and an 'analyzer' grating as described herein, results in a structure of relatively significant size as well as sub-optimal quantum efficiency (QE). It would also be beneficial to improve angular acuity and reduce the wavelength dependence of the previously embodied ASPs. Accordingly there is a need for an improved ASP apparatus and associated systems and methods that address these problems and concerns without compromising basic function or CMOS manufacturing capability.

SUMMARY

Embodiments of the invention are directed to apparatus and methods for measuring a light field at a given image plane. Pixel and detector devices disclosed herein are sensitive to both the intensity and the incident angle of incident light from an object scene. The disclosed apparatus and methods utilize the Talbot effect of periodic light diffracting structures to characterize incident light by its magnitude and direction. In certain aspects, local, micron-scale diffraction gratings at each of a large number of sensor sites are used to capture this information. To distinguish certain of these devices from the typical pixels of digital image sensors, we refer to them herein as "angle-sensitive pixels" (ASPs).

An embodiment of the invention is an angle-sensitive pixel device manufactured entirely in a standard CMOS fabrication process. In a non-limiting aspect, the ASP device includes a device support structure; a first periodic, light diffracting structure having a period, $p_1$, disposed in or on a top surface of the support structure; a second periodic structure having a period, $p_2$, oriented parallel to the first periodic structure and disposed in the support structure at a selected distance below the first periodic, light diffracting structure. As used herein, m, n are positive integers, $\lambda$ is the wavelength of a monochromatic, plane, incident wavefront on the first periodic, light diffracting structure, and $p_1$ is equal to or greater than $\lambda$. In an aspect, $p_1$ is equal to $p_2$. According to an aspect, the second periodic structure further includes at least two sets of at least two interleaved diffusion-type diodes, which could be finger diodes. The sets of diodes are, respectively, laterally displaced from the first periodic, light diffracting structure by a distance $np_1/m$, where n can have the values 0, 1, 2, 3, 4, 5, 6, 7, 8 and m can have the values 2, 3, 4, 8. The sets of interleaved diodes are disposed at a selected distance, $z_{TT}=(m_1/n_1)(2p_1^2/\lambda)$, below the first periodic, light diffracting structure and the second periodic structure.

An embodied micron-scale device requires both a periodic diffracting structure to generate Talbot self-images and a structure for analyzing these self-images. By sizing the entire device to fit within an area of at most tens of microns on a side, spatial resolution may be achieved that is comparable with existing image sensors. In an illustrative aspect, the periodic diffracting structure will have several periods within this area to produce an operable periodic self-image. Thus the diffracting structure may have a period of only a few wavelengths. Contemporary planar photolithography techniques can easily achieve the resolution required to generate appropriate diffracting structures. Numerical modeling and simulation can accurately predict behavior for finite gratings built on a single-micron scale.

According to a general embodiment, the structure for analyzing the self-images generated by the periodic diffracting structure may be an integrated light detector; for example, at least two, periodic, interleaved sets of at least two diffusion-type diodes as are well known in the art. According to further embodiments described herein below, the structure for analyzing the self-images may be one or more layers of periodic structures followed by a sensor in the form of at least two, periodic, interleaved sets of diffusion-type diodes, one or more single, large, well-type diodes known in the art, or a combination of the interleaved diffusion diodes disposed (and partially enclosed) in the one or more single, large, well-type diodes. The one or more layers of periodic structures may or may not be arranged co-perpendicularly.

An embodiment of the invention is a lens-less, angle-sensitive pixel (ASP) device that includes a device support structure; a first periodic, light diffracting structure having a period, $p_1$, disposed in or on a top surface of the support structure; a second periodic structure having a period, $p_2$, oriented parallel to the first periodic, light diffracting structure and disposed in the support structure at a selected distance below the first periodic, light diffracting structure; and a sensor disposed in the support structure at a selected distance below the first periodic, light diffracting structure and the second periodic structure.

An embodiment of the invention is a lens-less light-field detector that includes a detector support structure; a first pixel device, and a second pixel device disposed linearly adjacent the first pixel device. The first pixel device comprises a first periodic, light diffracting structure having a period, $p_1$, disposed in or on a top surface of the support structure; a second periodic structure having a period, $p_2$, oriented parallel to the first periodic, light diffracting structure and disposed in the support structure at a selected distance below the first periodic, light diffracting structure, wherein the second periodic structure is not laterally displaced from the first periodic, light diffracting structure; and a first sensor disposed in the support structure at a first selected distance below the first periodic, light diffracting structure and the second periodic structure. The second pixel device comprises a first periodic, light diffracting structure having a period, $p_1$, disposed in or on a top surface of the support structure; a second periodic structure having a period, $p_2$, oriented parallel to the first periodic, light diffracting structure and disposed in the support structure at the selected distance below the first periodic, light diffracting structure, wherein the second periodic structure is laterally displaced from the first periodic, light diffracting structure by an amount $(m_2/n_2)p_1$; and a second sensor disposed in the support structure at the first selected distance below the first periodic, light diffracting structure, wherein m, n are positive integers, $\lambda$ is the wavelength of an monochromatic, plane, incident wavefront on the first periodic, light diffracting structure, $p_1$ is greater than $\lambda$. According to an aspect, the first and second pixel devices further comprise a first intermediate periodic, light diffracting structure having a period, $p_1$, disposed between the first periodic, light diffracting structure and the second periodic structure, oriented perpendicularly to the first and second periodic structures; and a second intermediate periodic, light diffracting structure having a period, $p_2$, disposed between the second periodic structure and the first and second sensors, oriented perpendicularly to the first and second periodic structures, wherein in the first pixel device, the first and second intermediate periodic, light diffracting structures are not laterally displaced from the respective first and second periodic structure, further wherein in the second pixel device, the first and second intermediate periodic, light diffracting structures are laterally displaced from the respective first and second periodic structures by an amount $(m_2/n_2)p_1$. According to an aspect, the detector further comprises at least an $n^{th}$ ($n\geq3$) pixel device disposed linearly adjacent the ($n^{th}-1$) pixel device, including a first periodic, light diffracting structure having a period, $p_1$, disposed in or on a top surface of the support structure; a second periodic structure having a period, $p_2$, oriented parallel to the first periodic, light diffracting structure and disposed in the support structure at the selected distance below the first periodic, light diffracting structure, wherein the second periodic structure is laterally displaced from the first periodic, light diffracting structure by an amount $(m_n/n_n)p_1$, where $(m_n/n_n)>(m_{n-1}/n_{n-1})$; and an $n^{th}$ sensor disposed in the support structure at the first selected distance below the first periodic, light diffracting structure. In a further aspect, every $n^{th}$ ($n\geq3$) pixel device further comprises a first intermediate periodic, light diffracting structure having a period, $p_1$, disposed between the first periodic structure and the second periodic structure, oriented perpendicularly to the first and second periodic structures; and a second intermediate periodic, light diffracting structure having a period, $p_2$, disposed between the second periodic structure and the $n^{th}$ sensors, oriented perpendicularly to the first and second periodic structures, wherein in every $n^{th}$ ($n\geq3$) pixel device, the first and second intermediate periodic, light diffracting structures are laterally displaced from the first periodic structure by an amount $(m_n/n_n)p_1$, where $(m_n/n_n)>(m_{n-1}/n_{n-1})$.

Another embodiment of the invention is a lens-less light field imaging device comprising a two-dimensional, M×N array of ASP-light-field detectors as set forth herein, where M, N are integers equal to or greater than one.

According to all of the foregoing embodiments, the periodic diffracting structures may be of various forms including, but not limited to, diffraction gratings, parallel wire arrays, Ronchi rulings, phase gratings, and others well known in the art. Diffracting apertures may be in the form of slits or other aperture shapes, or mismatched refractive indices. Gratings may advantageously be made of metal or, in the case of phase gratings, CMOS process-compatible materials (e.g., silicon dioxide). The sensor(s) may be, without limitation, reverse-bias p-n junction diodes, forward-biased diodes, p-i-n diodes, charge-coupled devices (CCDs), single-photon avalanche diodes, or pairs of interleaved N+/p-substrate diffusion diodes. A device may incorporate one or more color filters if, for example, the incident light has a broad spectrum that may advantageously be narrowed.

An embodiment of the invention is an angle-sensitive pixel (ASP) device, comprising a substrate, a phase grating having a period, $p_1$, disposed in the substrate, wherein the phase grating is characterized by a periodic variation of refractive index in a direction transverse to an incident light field and forms a periodic intensity pattern in a Talbot plane below the phase grating, an amplitude transmission analyzer grating disposed in the Talbot plane, and a sensor disposed at a selected distance below the analyzer grating. In various non-limiting, exemplary aspects:
  the ASP device further comprises a dispersive material patterned over the phase grating;
  the phase grating comprises silicon dioxide;
  the sensor comprises at least one pair of interleaved N+/p-substrate diffusion diodes.

An embodiment of the invention is an angle-sensitive pixel (ASP) device, comprising a substrate, a phase grating having a period, $p_1$, disposed in the substrate, wherein the phase grating is characterized by a periodic variation of refractive index in a direction transverse to an incident light field and forms a periodic intensity pattern in a Talbot plane below the phase grating, and a sensor disposed at a selected distance below the analyzer grating. In various non-limiting, exemplary aspects:
  the ASP device further comprises a dispersive material patterned over the phase grating;
  the phase grating comprises silicon dioxide;
  the sensor comprises at least one pair of interleaved N+/p-substrate diffusion diodes.

Another embodiment of the invention is a light field imaging device comprising a two-dimensional, M×N array of ASP devices each including a phase grating with and without an analyzer grating, as outlined above, where M, N are integers equal to or greater than one, and a sensor.

An embodiment of the invention is directed to a method for determining a direction of incident light from an object, comprising creating a periodic, interference pattern of the incident light from the object, detecting the interference pattern and, determining a phase shift of the pattern relative to a reference position based upon the relative illumination of different diodes.

Embodiments of the invention thus pertain to imaging devices and methods that can enable extraction of information relating to the three-dimensional structure of the object light. Each ASP in the type of imager described herein may extract the incident angle of light as well as its brightness. Individual ASPs may be used to localize one or more light sources (such as for sun tracking, for example). When many such ASPs are combined in an array, such information may be used to reconstruct three-dimensional surfaces, or multiple distinct points in 3-D space, which may have application in, e.g., biological imaging. An imaging device according to embodiments of the invention may advantageously be built in a standard semiconductor manufacturing process such as those used to build microprocessors and present day digital camera imagers; for example, standard CMOS fabrication processes.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

BRIEF DESCRIPTION OF THE DRAWINGS

FIG. 17a shows a top cross sectional plan view of a full interleaved diode light-field sensor cell according to an exemplary embodiment of the invention; FIG. 17b shows a top cross sectional plan view of a full interleaved diode light-field sensor cell according to an exemplary embodiment of the invention; FIG. 17c shows a top cross sectional plan view of a full interleaved diode light-field sensor cell according to an exemplary embodiment of the invention;

FIG. 27a schematically illustrates the manufacturing of a phase grating in standard CMOS without added masks and a cross section view of a chip as manufactured, in which top two metal layers have been used as etchstop layers. Both direct interleaved diode ASPs (bottom) and analyzer grating ASPs (top) can be made; FIG. 26b schematically illustrates applying an anisotropic oxide etch, which removes oxide insulator until metal is exposed; FIG. 26c schematically illustrates removal of the metal etchstop to produce the desired phase grating structures above the photosensors; FIG. 26d schematically illustrates coating the surface with a material with a distinct refractive index that provides an additional parameter in grating design, according to an illustrative embodiment of the invention;

DETAILED DESCRIPTION OF NON-LIMITING, EXEMPLARY EMBODIMENTS OF THE INVENTION

Reference will now be made in detail to the present exemplary embodiments of the invention, examples of which are illustrated in the accompanying drawings.

Embodiments of the invention are directed to angle-sensitive pixel devices and light field image detectors incorporating these ASP devices to measure both the intensity and the incident angle of incident light, and associated methods. The disclosed apparatus and methods utilize the Talbot effect.

Figure 2A:
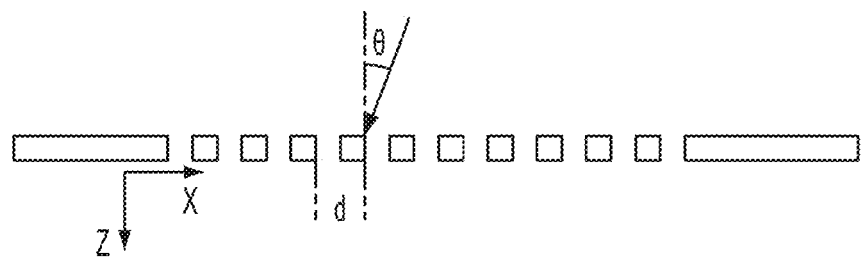
FIG. 2a is a cross sectional, schematic view of a diffraction grating with a definition of scale and dimensions.
Figure 2B:
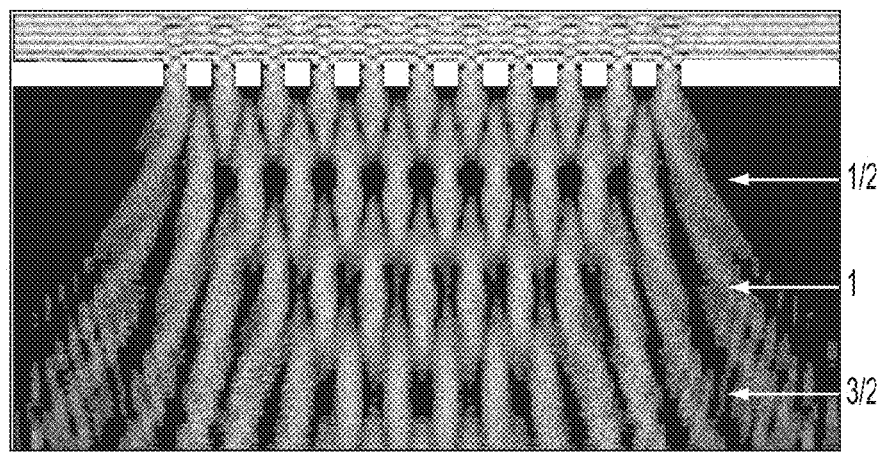
FIG. 2b shows FDTD simulations of the Talbot effect for light normally incident on the grating, and the self images at multiples of the ½ Talbot depth.

The Talbot effect, or the self-imaging property of periodic objects such as diffraction gratings, was first discovered by Henry Fox Talbot in 1836. When an infinite diffraction grating is illuminated by a plane wave normal to its surface, identical images of the grating are formed at certain equally spaced distances behind the grating. FIG. 2a diagrammatically illustrates the parameters of a diffraction grating with incident light (nominally 500 nm wavelength) striking the grating at normal incidence and at a θ=5 degree incident angle. The Talbot effect is a consequence of Fresnel diffraction, and the interference image (diffraction pattern) indicated at arrow 1 as shown in FIG. 2b, forms at integer multiples of the Talbot distance $z_T=2d^2/\lambda$, where d is the period of the grating and λ is the wavelength of incident light. Additional, more complex sub-images can be observed at the fractional Talbot distances $z=(m/n)z_T$ (indicated at arrows ½, 3/2), where m and n are positive integers.

A property of the Talbot effect is its response to off-axis illumination. For macroscopic (d>>λ) linear gratings illuminated by an off-axis plane wave incident at angle θ, self-imaging is observed at multiples of the distance $z=2\cos^3(\theta)d^2/\lambda$. Furthermore, the images exhibit a lateral shift $\Delta x=z\tan(\theta)$ perpendicular to the grating lines as a result of the off-axis wave propagation.

Multiple sources of off-axis illumination each generate their own set of laterally shifted grating self-images, and these self-images superpose. For small angles, these self-images all form at approximately the same distances, and the superimposed image contains information about the magnitude of illumination as well as direction. The incident angles of light rays striking the grating can be determined by measuring the shift in Talbot self-images.

Figure 2C:
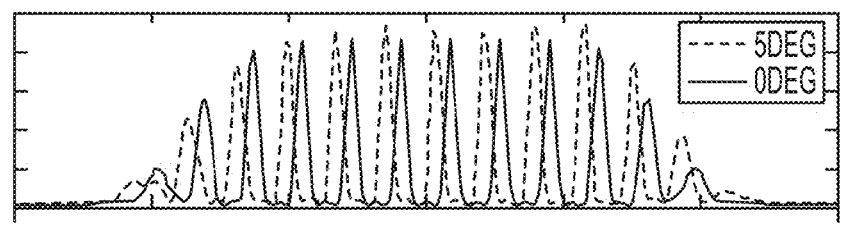
FIG. 2c is a plot based on an FDTD simulation showing the lateral shift of the self image at the ½ Talbot depth with shifting incident angle from θ=0° to 5°, according to an illustrative embodiment of the invention.

FIG. 2c graphically shows the light intensity of the Talbot images at a diode plane for normally incident light and light incident at θ=5 degrees. The lateral shift of the diffraction patterns changes with incident angle.

Modern semiconductor manufacturing of standard CMOS circuits allows for the construction of very fine features, on the order of a single wavelength of light, and so allows for the construction of metal diffraction gratings and photodiode arrays that are smaller than the wavelength of visible light. To generate the Talbot effect in a standard CMOS layer stack, the self-images need to form within microns of the diffraction grating. This may require the diffraction grating to have a period of only a few wavelengths. Conventional analyses of diffraction are invalid at these dimensions; however, numerical simulations such as those used to generate FIG. 2, confirm that, even for these geometries, diffraction generates Talbot-like self-images at regular distances. These periodic intensity patterns retain incident angle sensitivity.

The challenge, then, is to extract shifts in these periodic intensity patterns using structures on a pixel scale. For macroscale applications, the simplest approach to measuring these shifts is to place a small array of CCD or CMOS photosensors at the plane of self-image formation. The array captures the self-image directly, which can be used to determine the angle and intensity of incident light. At the microscale, however, the penetration depth of light in silicon limits the resolution of photodiodes to about 1 µm, making it difficult to resolve sub-micron features of the self-image.

A micron-scale light-field imager device requires both a Talbot self-image generator and a structure that can analyze these images. In order to achieve spatial resolution comparable with existing image sensors, the entire device structure must fit within an area that is at most tens of microns on a side. To produce a reasonably periodic self-image, the grating must have several periods within this area. Together these two constraints suggest using a grating with a period of only a few wavelengths. Contemporary planar photolithography techniques can easily achieve the resolution required to generate appropriate diffraction gratings. Numerical modeling and simulation can accurately predict behavior for finite gratings built on a single-micron scale.

Numerical treatments show that as long as the period is greater than the wavelength of incident light, Talbot-like self-images can be observed in close proximity to a diffraction grating. We have performed simulations using the finite-difference time domain (FDTD) technique and observed patterns as shown in FIGS. 2b and 2c. In particular, starting from the ½ Talbot distance, we observe strong intensity patterns with periodicity identical to the diffraction grating. Additional simulations show that under off-axis illumination, the intensity patterns generated by the high-density gratings shift laterally. An effect of moving to wavelength-scale diffraction gratings is to suppress higher-order fractional Talbot images.

To extract incident angle information about the Talbot pattern, it is necessary to characterize the horizontal offset of the self-images. Previously reported work used gratings (and self images) that were significantly larger (pitch of d=250 µm) than the pixels of the image sensor itself. Thus the image sensor array could directly capture the self-image as a set of electrical signals. However, in a micron-size device according to an aspect of the invention, the high density imager array would require a pixel pitch of ¼ the grating pitch (e.g., on the order of 200 nm) to effectively resolve the features of the Talbot image. Although sub-micron photo-sensors can be built, the images they capture tend to be blurred by diffusion effects, limiting their actual resolution to 1 µm or worse.

Figure 3A:
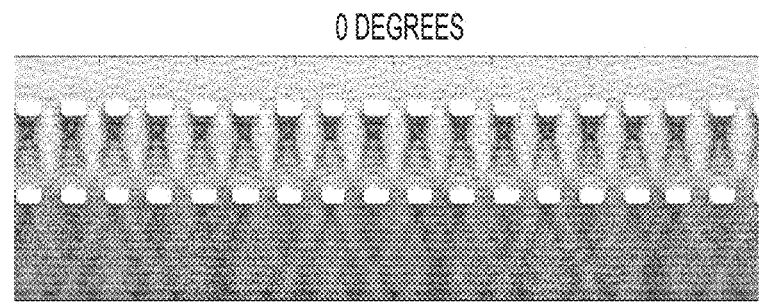
FIG. 3a shows FDTD simulations illustrating the effect of including an analyzer grating at the ½ Talbot depth when the peaks of the self-image align with the bars of the analyzer grating, little light passes through to a light detector below.
Figure 3B:
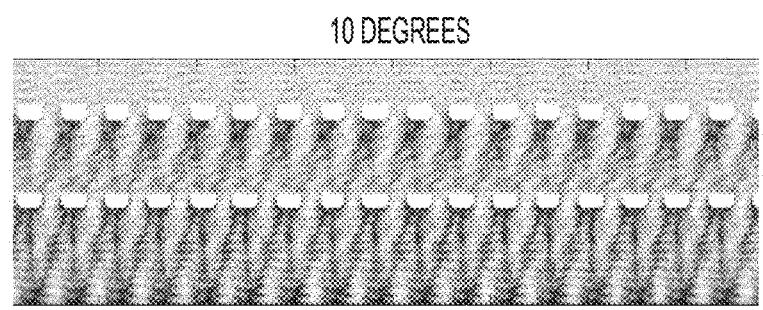
FIG. 3b shows simulations illustrating the effect of including an analyzer grating at the ½ Talbot depth when the incident angle is shifted so that the peaks align with gaps in the analyzer grating, much more light passes to the detector.
Figure 3C:
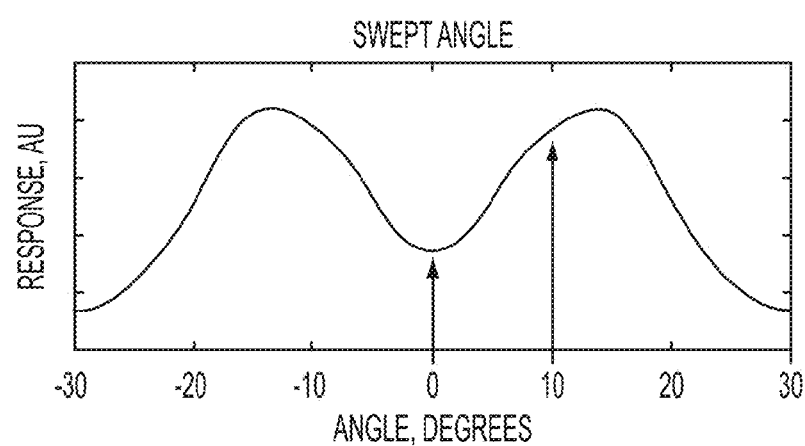
FIG. 3c shows simulations illustrating the effect of including an analyzer grating at the ½ Talbot depth of detected light changes periodically with swept incident angle, according to an illustrative embodiment of the invention.

A solution provided by an embodiment of the invention includes a second parallel analyzer grating 304 of identical period to the first grating 302 disposed at the self-image plane, as illustrated in FIGS. 3a, 3b. The second (analyzer) grating 304 uses the Moiré effect to filter the Talbot image. When the intensity peaks align with gaps in the second grating as shown in FIG. 3b, light passes through the analyzer grating 304. When the intensity peaks are out of alignment (FIG. 3a), the bars of the analyzer grating block the light. By placing a single large photosensor under the analyzer grating and measuring the total light flux, we can extract the alignment of the self-image with the analyzer grating (FIG. 3c).

Figure 4A:
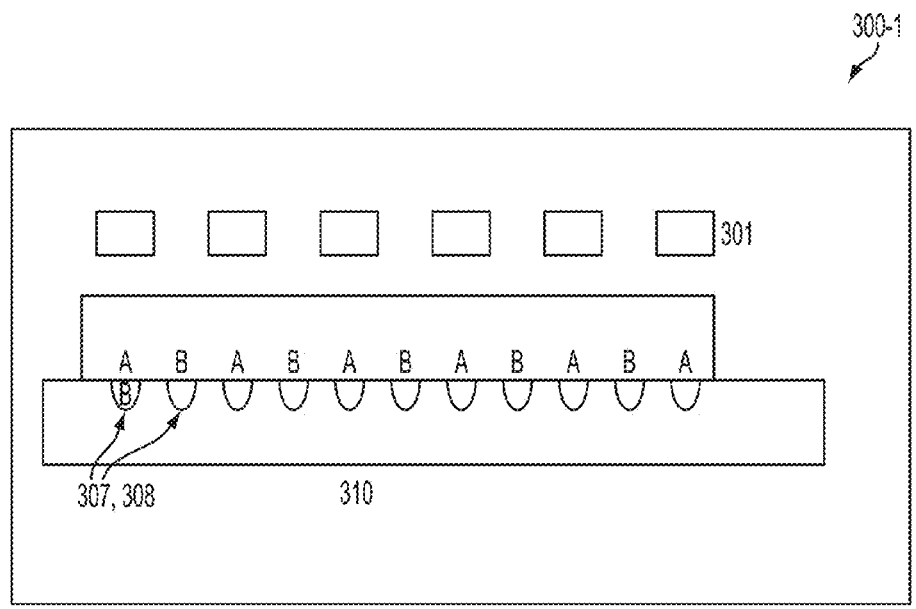
FIGS. 4a, b diagrammatically show structures for extracting information about diffraction pattern phase according to alternative, exemplary aspects of the invention.
Figure 4B:
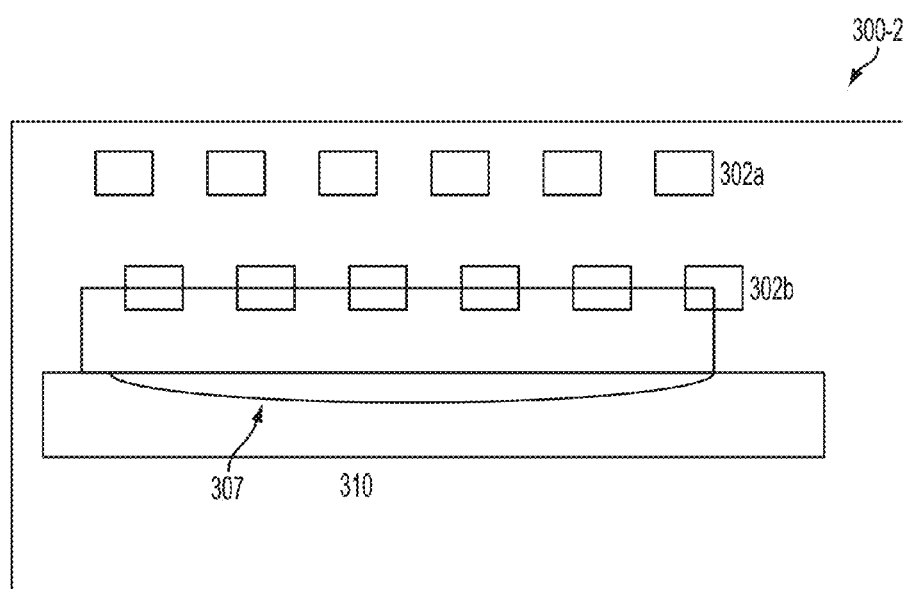

FIG. 4b shows an exemplary, diagrammatic illustration of such a structure embodiment 300-2 for extracting partial information about the diffraction pattern phase. Two metal gratings 302a, 302b are placed at a 90 degree lateral offset relative each other over a single, large well-diode 307 integrated into substrate 310. Separate pixels with gratings shifted by 0, 180 and 270 degrees or, alternatively, 0, 120 and 240 degrees, for example, would extract full angle information. This approach decouples the design of the diodes from that of the gratings, allowing for better diodes. Also, because the finest features in this aspect are the gratings themselves rather than the photodiodes, the same class of structure can be built using lower resolution photolithography (i.e., in a larger feature size, cheaper manufacturing process).

Figure 5A:
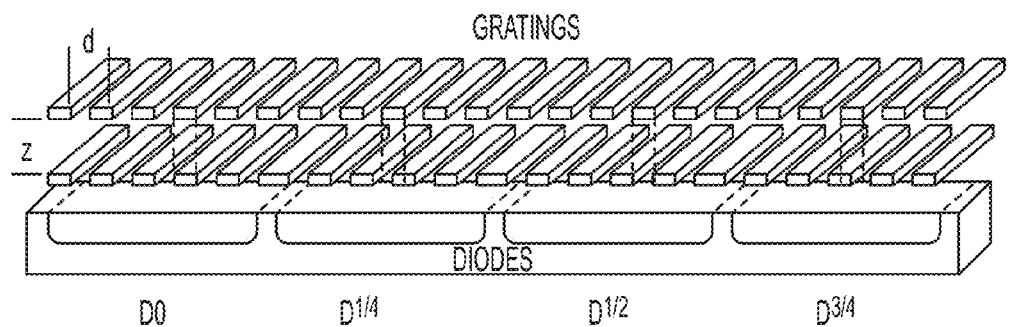
FIG. 5a illustrates an ASP device having multiple, adjacent, single deep-well photodiodes and stacked, offset gratings disposed above (black dotted lines illustrate relative alignment of the gratings.

The total light flux detected is dependent on both the overall source brightness and the incident angle. This may lead to an ambiguity between intensity and angle in the sensor output, since a bright source at a blocked angle yields the same sensor output as a dimmer source at an angle passed by the analyzer grating. To disambiguate angle and intensity, in accordance with an aspect of the invention as illustrated in FIG. 5a, a detector 400-2 includes n (n=4 as shown) single well-diode sensors $407_n$ integrated in substrate 410, and two stacked gratings 402a, 402b disposed above in close proximity so that they see approximately the same light field. Each diode has a different relative offset between the analyzer grating 402b and the image-generating grating 402a. Using the unique signals produced by each of the set of sensors, one can recover intensity and incident angle.

Figure 5B:
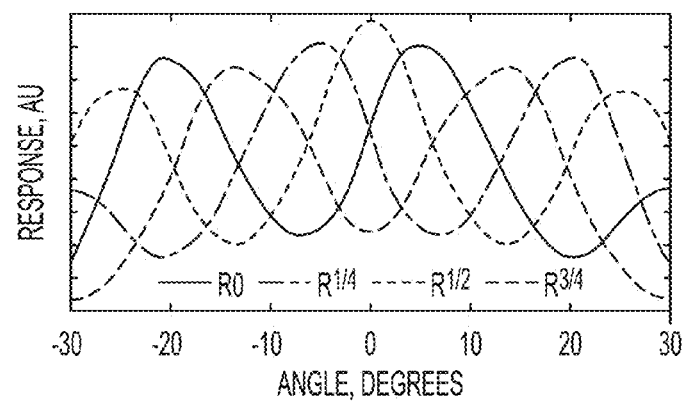
FIG. 5b shows simulation results for various offsets: note that the incident angles that generate peak responses shift proportionally with the offset of the grating, according to an embodiment of the invention.

Simulated responses for one set of four sensors under plane illumination of different angles are shown in FIG. 5b. It is seen that the transmission through the analyzer grating is periodic in incident angle due to the lateral shift of the periodic self-images. The responses of these sensors can be approximately modeled by the equations:

$$R_0 = I_0(1 - m\cos(b\theta))F(\theta)$$

$$R_{1/4} = I_0(1 + m\sin(b\theta))F(\theta)$$

$$R_{1/2} = I_0(1 + m\cos(b\theta))F(\theta)$$

$$R_{3/4} = I_0(1 - m\sin(b\theta))F(\theta) \quad (1)$$

where $I_0$ is proportional to incident intensity, $\theta$ is incident angle, m is a measure of the modulation depth, and b is a measure of angular sensitivity. $F(\theta)$ is an even-symmetric function included to account for surface reflections and other effects that reduce responses to high angle incident light independent of angular sensitivity.

From the four outputs in equation 1, it is possible to determine the intensity and incident angle (in the x-z plane) of light. Summing the ASP responses $R_0$ and $R_{1/2}$ (or $R_{1/4}$ and $R_{3/4}$) removes the modulation produced by incident angle and provides information on overall intensity.

$$I_0 F(\theta) = \frac{R_0 + R_{1/2}}{2} = \frac{R_{1/4} + R_{3/4}}{2} \quad (2)$$

Incident angle can be extracted as:

$$\theta = \frac{1}{b}\tan^{-1}\left(\frac{R_{1/4} - R_{3/4}}{R_{1/2} - R_0}\right) \quad (3)$$

Figure 6A:
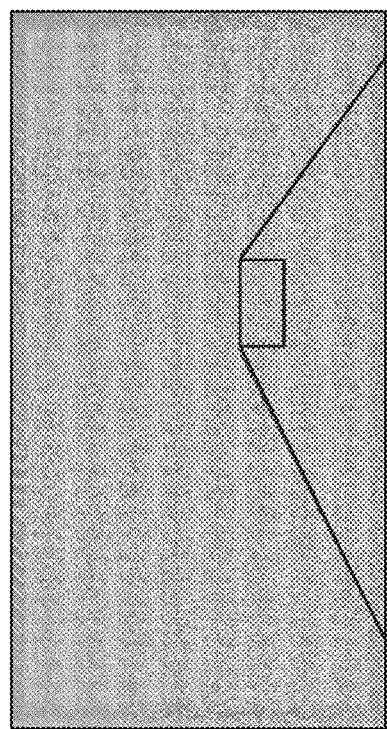
FIGS. 6 a, b are microphotographs of a) one ASP, and b) an 8×8 array of ASPs, manufactured in 130 nm CMOS, according to an embodiment of the invention.
Figure 6B:
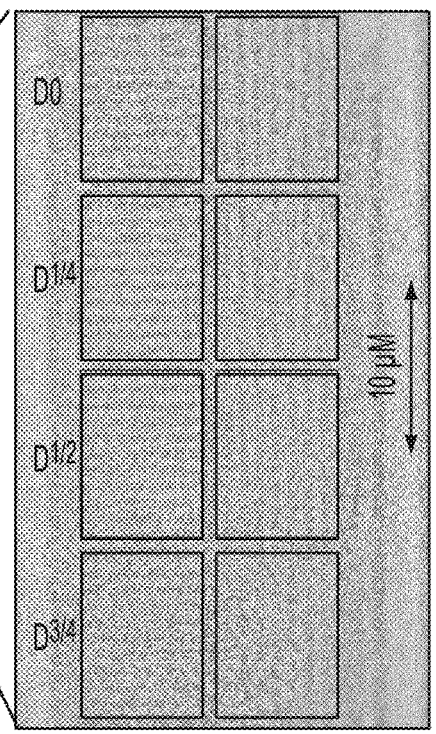

Because the lateral shift of the Talbot images is observed only for off-axis illumination at angles perpendicular to the grating lines, the device 400-2 is responsive only to angles in one direction. In order to obtain full illumination angle information, a second set of identical devices with gratings rotated by 90 degrees, in close proximity to the first, were provided. This second set is responsible for measuring the angle information ignored by the first set of sensors. A complete angle-sensitive pixel (ASP) 500-1 composed of eight different sensors placed in close proximity is shown in FIG. 6b. Four sensors are responsible for the angle in the x-z plane; four more are needed for the angle in the y-z plane. For both x-z and y-z gratings, diffraction-analyzer offsets of 0, d/4, d/2 and 3d/4 were used. The analyzer gratings were positioned at the ½ Talbot distance, the smallest distance where self-images with periodicity identical to the diffraction grating are found. An 8×8 ASP array light field image sensor 500-2 manufactured in a digital 130 nm CMOS fabrication process is illustrated in the photomicrograph of FIG. 6a.

The overall size of the exemplary eight-sensor ASP 500-1 is 20 µm by 40 µm, with each individual sensor being 10 µm square. The stacked diffraction gratings were built in wiring layers, above intrinsic p-n junction photodiodes. In this illustrative example, each grating in each of the eight sensors was a Ronchi ruling (equal width bars and gaps) using copper bars with a period of 880 nm. All other space was filled with silicon dioxide. One set of gratings was used to bus out the data generated, which eliminated the need for wiring lanes in the array. As the gratings provide a large number of bus lines, the eight ASP outputs are read in parallel. The grating separation, z, was limited by available interconnect layer spacing, and pitch, d, chosen from numerical simulations to maximize modulation depth, m, for green (525 nm in vacuum, 350 nm in oxide) light. For the device 400-2 shown in FIG. 5a, empirical simulations for green ($\lambda$=525 nm in vacuum) light determined the ½ Talbot distance in silicon dioxide to be 2 μm. The top diffraction grating was positioned in the 6th metal layer and the analyzer grating in the 3rd metal layer, for a separation of 2 microns. A single p-n photodiode in each of the eight sensors measured the total light flux through the stacked gratings. A standard 3T active pixel sensor was used to buffer the photodiode outputs, and several multiplexers allowed access to each ASP individually.

Figure 7:
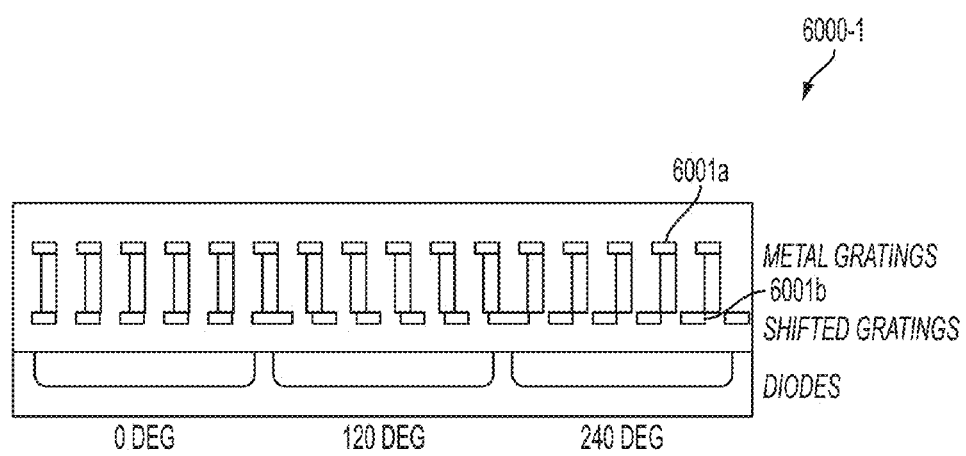
FIG. 7 is a diagrammatic cross sectional view of an image sensor according to an alternative aspect of the invention.

FIG. 7 shows an illustrative aspect of a device embodiment 6000-1 similar to that shown in FIG. 5a in which three single diodes 6007, 6008, 6009 are disposed adjacent two grating layers 6001a, 6001b. Second grating layer 6001b is shifted relative to grating 6001a by 0, ⅓ and ⅔ of the grating period.

Figure 8:
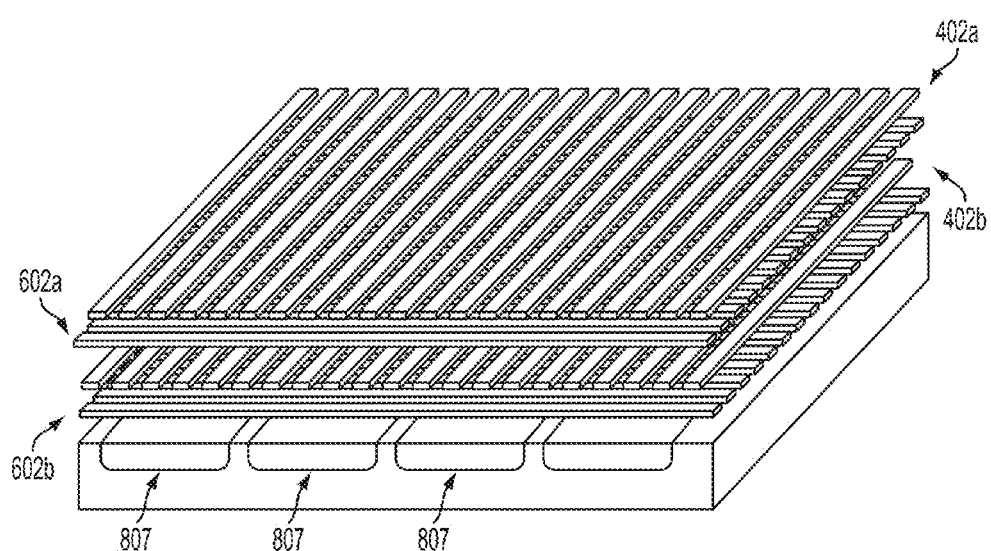
FIG. 8 is a perspective view of an ASP-based light field image device according to an embodiment of the invention.

According to an alternative aspect, a light field image detector 600-1 is illustrated in FIG. 8. In this aspect, a second set of gratings 502a, 502b rotated by 90 degrees and interleaved between grating 402a, 402b are provided in close proximity thereto. This second set of gratings is responsible for measuring the angle information ignored by the first set of sensors.

To test our ASP, a light source (commercial green LED, with center wavelength of 525 nm and spectral width of 32 nm) was mounted on a variable angle arm at a fixed distance from the fabricated arrays. No additional collimation or filtering was performed, as a non-ideal illumination source better approximates real-world imaging applications. When a range of wavelengths are present, the self-images observed are a superposition of the intensity patterns produced by each wavelength. The spectral width of the source is relatively narrow and the path length differences, which make the Talbot patterns, are shorter than the source's coherence length, so we did not expect significant deviation in performance from our monochromatic, coherent simulations.

Figure 9:
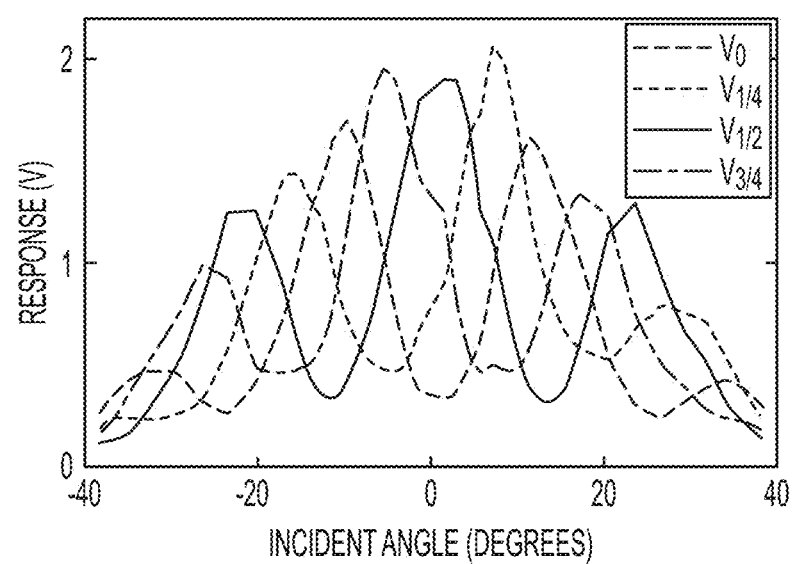
FIG. 9 is a graph showing measured responses of an ASP as incident angle is swept, according to an illustrative aspect of the invention.

We recorded the outputs of a single ASP for each angle as the source was moved. The outputs corresponding to one set of four sensors in the ASP are shown in FIG. 9. Reasonable agreement was obtained between measured results and those predicted by simulation. Fitting the curves in FIG. 9 with the model in equation (1) gives b=15 and m=0.7, with a root-mean-squared error of 9%. The second set of four sensors (for characterizing angles in the y-z plane) produced similar curves in response to changes in incident angle. Differences observed between measurement and idealized simulations such as those in FIGS. 2 and 3 are due to reflection off the silicon dioxide surface, manufacturing variation, and the finite gratings actually used. However, our simulations reasonably characterized the angular sensitivity and modulation depth of the ASP.

Fine-pitch gratings are known to polarize the light they transmit. A recent study on the polarization-dependent Talbot effect in high-density gratings predicts that gratings with period of approximately 2.5$\lambda$ should show significant polarization sensitivity. Specifically, the Talbot self-images formed at the ½ Talbot distance by TE (electric field parallel to the grating lines) polarized light should be approximately twice as bright as those formed by TM (magnetic field parallel to the grating lines) polarized light. Our observations are in good agreement with this prediction: when we rotated the polarization of the incident light on our ASP from TE to TM, the overall observed intensity decreased by a factor of 2.05. However, both angular sensitivity b and modulation depth m changed by less than 10%. These characteristics indicate that the TM-polarized Talbot self-images are weaker than the TE-polarized self-images, but otherwise behave similarly in their encoding of angle and intensity information.

Figure 10:
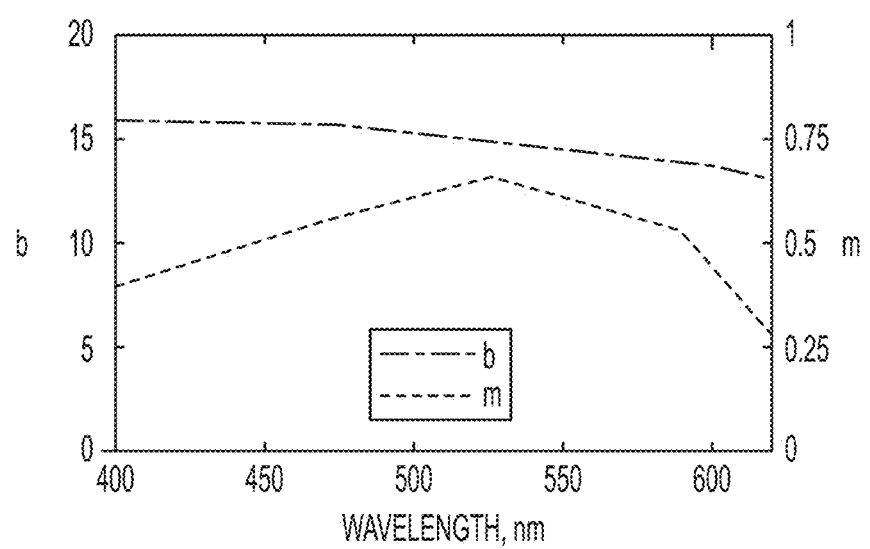
FIG. 10 is a graph showing the measured effect of wavelength on angular sensitivity, b, and modulation depth, m, according to an illustrative aspect of the invention.

The design was optimized for $\lambda$=525 nm, but we tested it across a range of wavelengths from 400 nm to 620 nm. We expected little change in angle sensitivity b in response to changes in wavelength, as the Talbot self-images do not change in periodicity with changes in $\lambda$. This prediction was born out by measurement, as can be seen in FIG. 10: b was only weakly sensitive to $\lambda$ over the range 400 nm to 620 nm. However, changes in wavelength significantly change the Talbot distances. The analyzer grating was not optimally positioned when $\lambda \neq 525$ nm, so the observed self-images were blurred, and modulation depth, m, degraded. Over this range of wavelengths, we recover angle information less efficiently, but the angle sensitive function does not vanish. The fact that the ASP works across such a range of wavelengths is a direct consequence of analyzing the self-image at the ½ Talbot distance, where the relative depth of the Talbot pattern is least sensitive to $\lambda$.

Figure 11A:
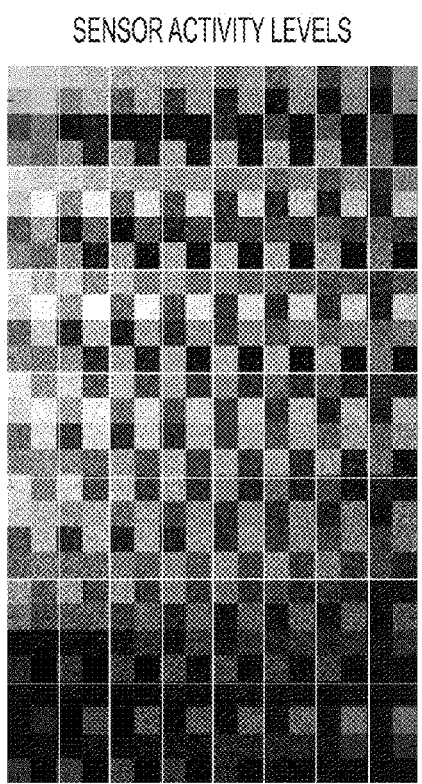
FIG. 11a shows the measured ASP array response to a light source held 500 µm above the array and slightly to the left and responses of individual sensors, where brighter squares represent more heavily illuminated sensors and white lines delimit individual ASPs.
Figure 11B:
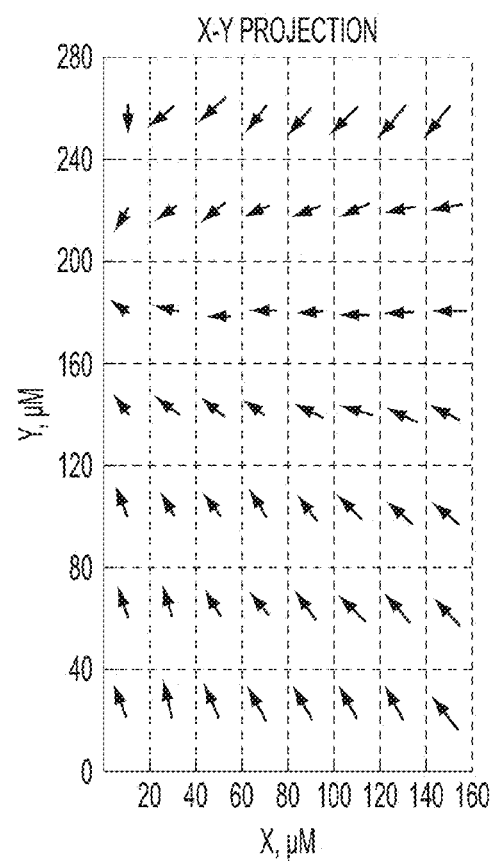
FIG. 11b shows the measured ASP array response to a light source held 500 µm above the array and slightly to the left and computed incident angle for each ASP (projected into the x-y plane), according to an illustrative aspect of the invention.

To confirm the light-field imaging capability of our sensors, we placed a multimode fiber tip 500 μm directly above the ASP array. After coupling light from a light emitting diode (identical to the one used in single ASP tests) into the fiber, light exiting the fiber will have a conical profile, and thus a simple divergent light field at the plane of the array. We recorded from all 64 sites on the ASP array and measured the output of each sensor, as shown in FIG. 11a. As can be seen, adjacent sensors tuned to different angles responded very differently, and their relative responses depend upon their overall location relative to the light source. Applying equation (3) and the angle response data shown in FIG. 9, we reconstructed the light vectors for each ASP, as shown in FIG. 11b.

Figure 12A:
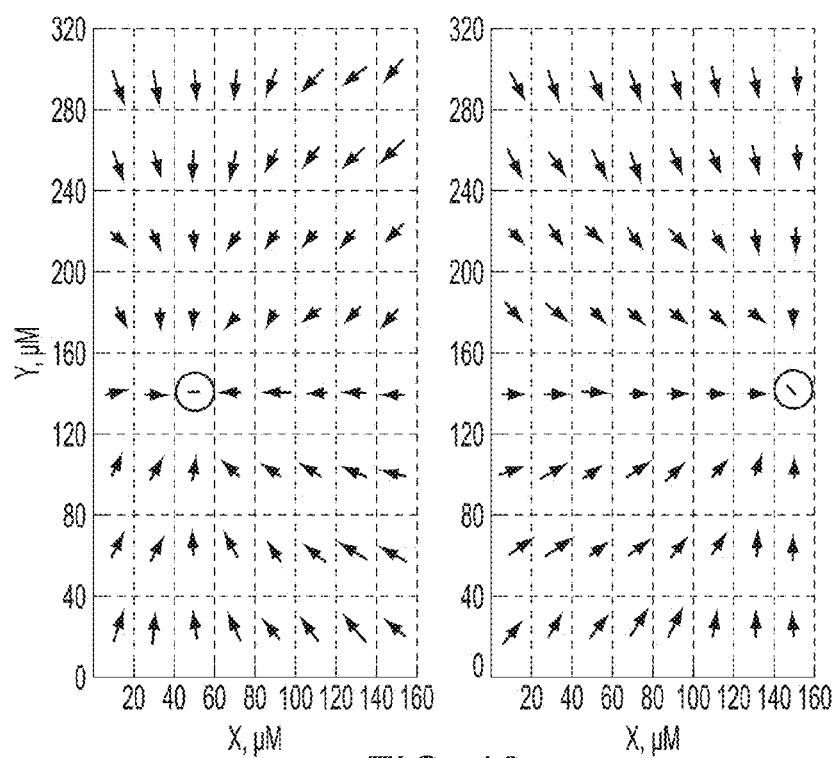
FIG. 12a shows how an 8×8 ASP array accurately resolves light source locations in 3-D space and the measured light-vector field due to a source 550 µm above the array can clearly reconstruct lateral shifts in location (in this case by 100 µm)
Figure 12B:
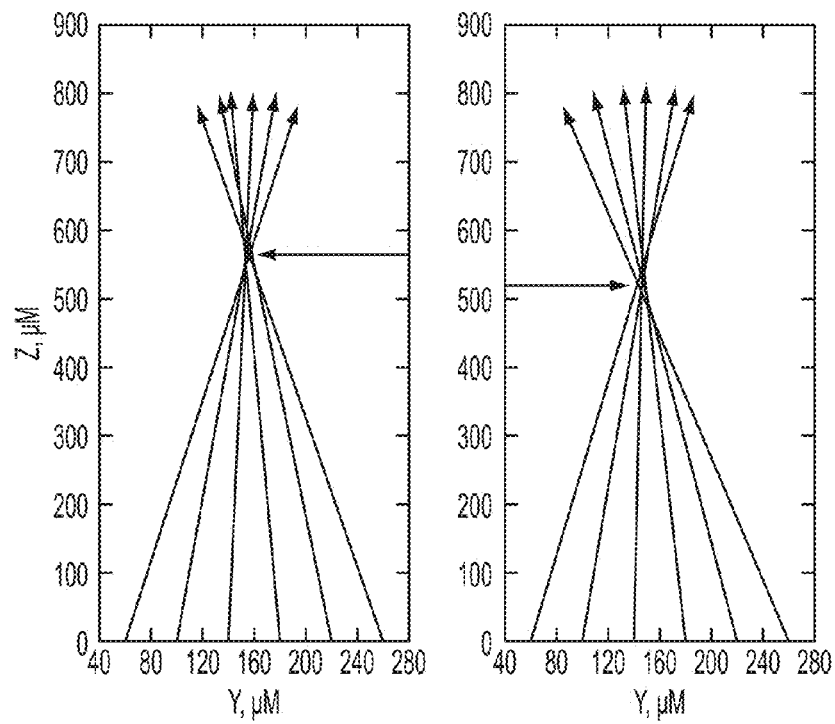
FIG. 12b shows how an 8×8 ASP array accurately resolves light source locations in 3-D space and measured light-vector field can also be used to reconstruct changes in depth (z) of a light source, in this case by 50 µm, according to an illustrative aspect of the invention.

To further confirm the capabilities of our array, we moved the light source to various locations in three-dimensional space above the array. At each position we recorded the sensors' responses and reconstructed the incident angle of light coming from the fiber. The array could be used to accurately reconstruct the location of the light source in two dimensions, as shown in FIG. 12a, where the source was moved by 100 μm in the x-direction, and the computed incident angles reflect this. More strikingly, the array could be used to accurately localize the light source in the third, z direction, accurately capturing a 50 μm shift in the height of the source above the array, as shown in FIG. 12b. Thus an array of ASPs is able to accurately reconstruct the three-dimensional structure of simple light sources, providing information beyond what is available from the intensity map available from a standard image sensor.

FIG. 4a shows a cross sectional schematic of a non-limiting exemplary device embodiment 300-1 of the invention. The device includes a metal slit grating 301 and a substrate 310 with multiple linear arrays of two integrated, interleaved fingered diodes (A) 307, (B) 308 that are relatively shifted by 180 degrees (i.e., offset by zero and one-half period of the grating) relative to the grating. Multi-finger diodes advantageously provide maximum photon capture.

Figure 13:
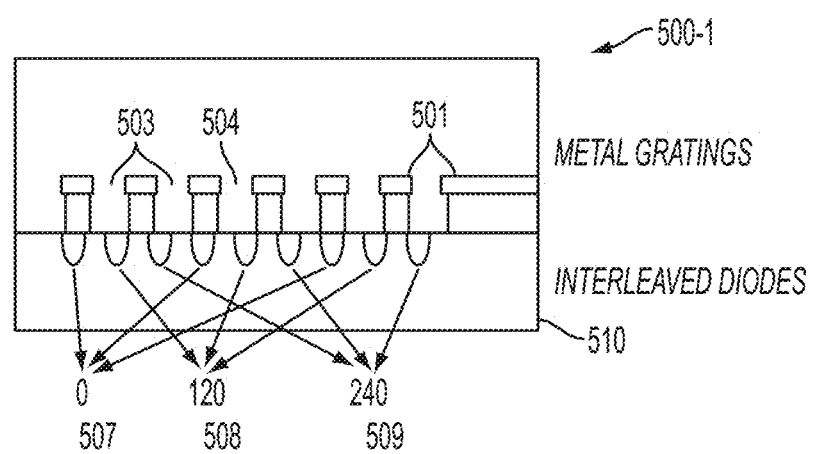
FIG. 13 is a diagrammatic cross sectional view of an image sensor according to an alternative aspect of the invention.

FIG. 13 shows an imaging device 500-1 based upon a three-diode structure according to a non-limiting exemplary embodiment of the invention. The device includes a metal transmission grating 501 having multiple, periodic slit apertures 503. The light shadings indicated by reference numeral 504 do not represent any physical part of the device, rather merely the alignment between the grating and the diodes. The device further includes a single structure of three linear arrays of three interleaved diodes, 507, 508, 509, integrated in a substrate 510. The three illustrated diodes of diode array 507 are aligned with the grating (no offset) and thus will detect a zero degree phase shift in the interference pattern (not shown). Similarly, the three illustrated diodes of diode array 508 are offset by ⅓ of the grating period and thus detect a 120 degree phase shift; while the three illustrated diodes of diode array 509 are offset by ⅔ of the grating period and thus detect a 240 degree phase shift.

Figure 14:
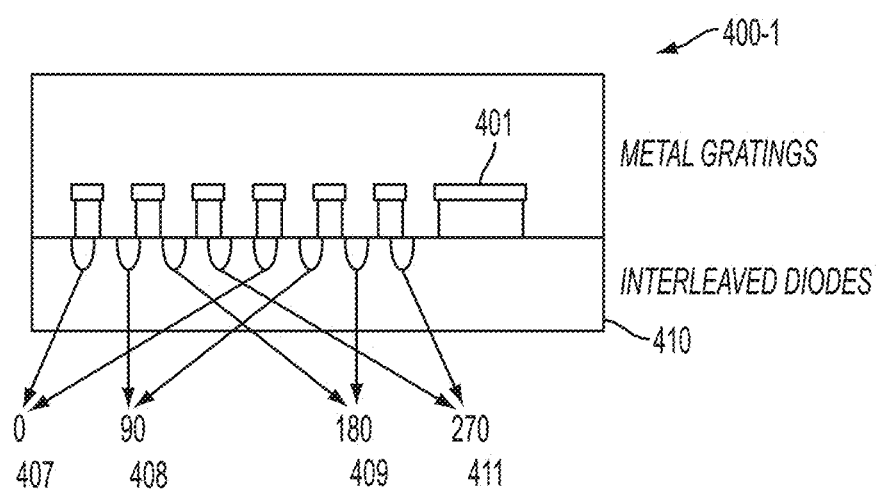
FIG. 14 is a diagrammatic cross sectional view of an image sensor according to an alternative aspect of the invention.

FIG. 14 shows an alternate device arrangement 400-1 of diodes and grating according to a non-limiting, exemplary embodiment. As shown in FIG. 14, an integrated, single-interleaved set of four diodes 407, 408, 409, 411 are positioned offset by zero, ¼, ½ and ¾ of the grating 401 period providing respective phase shifts of 0°, 90°, 180° and 270°. Note that the single-interleaved set of four diodes is different than, e.g., the two adjacent diode sets as shown in FIG. 4a. Again, the light shadow areas in the figure do not reflect any additional physical structure; rather, they only indicate alignment between diodes and metal.

Figure 15:
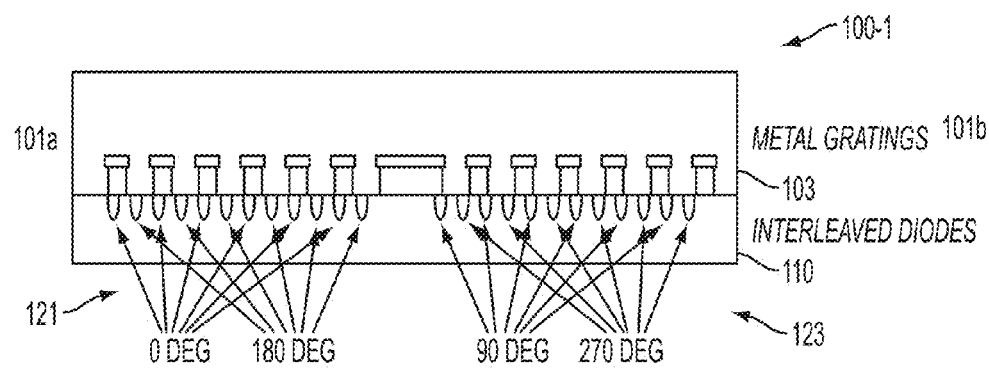
FIG. 15 is a diagrammatic cross sectional view of an image sensor according to an alternative aspect of the invention.

FIG. 15 shows a cross-sectional schematic of a detector device 100-1 according to an alternative, non-limiting exemplary embodiment of the invention. Sensor device 100-1 incorporates one set of interleaved diodes 121 at 0 and 180 degrees relative to the grating and another set of interleaved diodes 123 at 90 and 270 degrees. This type of arrangement may prevent diode overlap. The two shifted gratings 101a, 101b are shown as darkly shaded while the lighter shading 103 beneath each grating is presented merely to show the alignment between the grating and the diodes and does not represent any physical structure of the device.

Figure 16A:
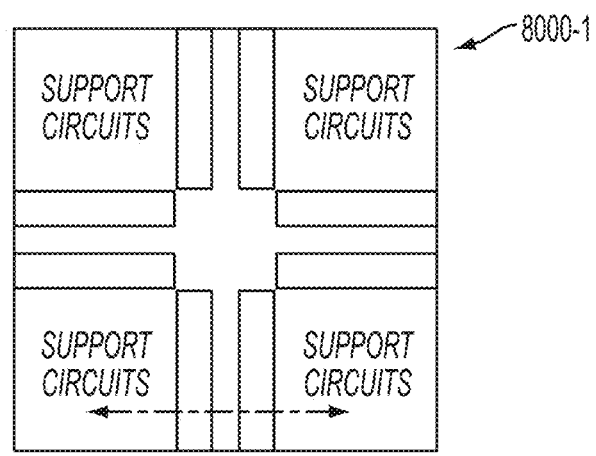
FIGS. 16a, 16b are, respectively, a top view and a cross sectional of an alternate imaging sensor according to an illustrative aspect of the invention.
Figure 16B:
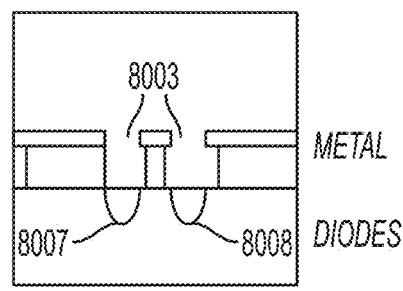

FIG. 16a shows a top view of components of a non-limiting, exemplary device aspect 8000-1 incorporating just two slits 8003 and two diodes 8007, 8008. FIG. 16b is a cross-sectional view through the dashed line in FIG. 16a. This design is compact, allowing for higher spatial resolution.

FIGS. 17(a-c) show top views of components of a non-limiting, exemplary full interleaved diode light-field sensor cell 5000-1, having gratings and diodes in both the vertical (5006a, b) and horizontal (5006c, d) orientations, which may be used to capture both azimuth and altitude information about the source object. FIG. 17a illustrates the layout of diodes (e.g., n-type diffusion in p-substrate), wherein each set of vertically-oriented diodes 5006a, b contains a pair 5002, 5004 of interleaved diode arrays and each set of horizontally-oriented diodes 5006c, d contains a pair 5008, 5010 of interleaved diode arrays. FIG. 17b shows the associated metal gratings 5001 with the same orientations as the corresponding diode arrays. As further shown in FIG. 17b, the vertically-oriented gratings may be used as a data bus to carry information from each column to the edge of the array at 5015 without giving up area in the imager itself. Alternatively, the gratings may be used to tie many individual diodes to processing circuits away from the array itself. This maximizes the photosensitive area of the imager, recovering area lost to circuits required to convert light into electrical signals. FIG. 17c shows an overlay of diodes and gratings shown in FIGS. 17a, b. FIG. 15, which shows a cross-section of the horizontally-oriented detectors (i.e., along the dashed black line in FIGS. 17a-c, illustrates that the relative alignment of the diodes and metal grating are shifted for the 0/180° cases versus the 90/270° case.

Figure 18:
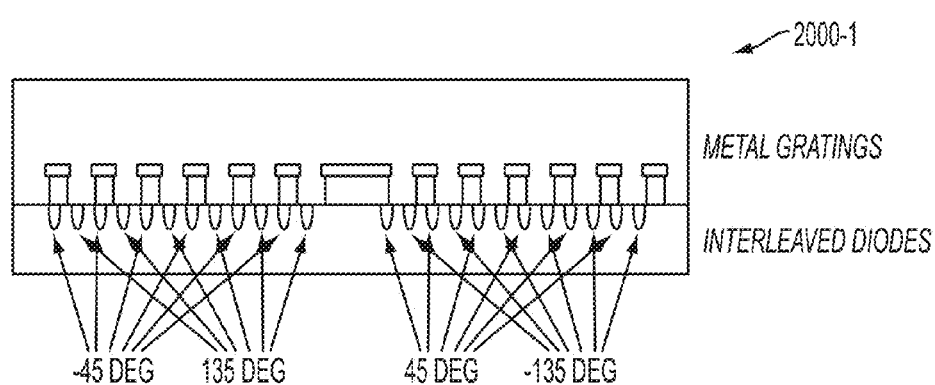
FIG. 18 is a diagrammatic cross sectional view in which all of the diodes are shifted by ⅛ of the metal grating pitch, according to an illustrative aspect of the invention.

FIG. 18 shows an exemplary device aspect 2000-1 similar to that of 100-1 except that all diodes are shifted by ⅛ of the grating pitch, representing phase shifts of −45°, 135°, 45° and −135°. This figure illustrates that the precise alignment of diodes and metal is less important than the relative alignment of diodes to each other. The ⅛ period shift should have no appreciable effect on the function of the structures disclosed herein. This insensitivity applies to all structures disclosed herein, and to the alignment of secondary gratings in the "double grating" embodiments described herein.

Figure 19:
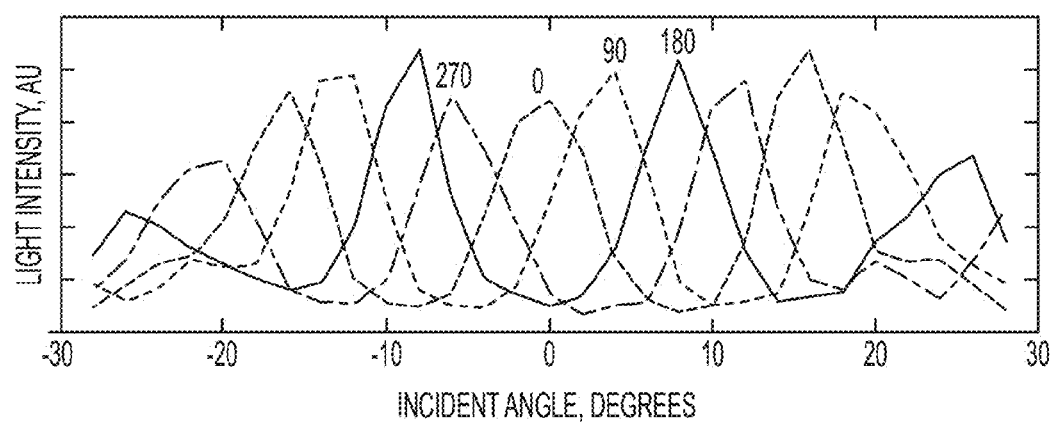
FIG. 19 graphically shows simulated photocurrents from four distinct diode arrays at 0, 90, 180 and 270 degrees relative to a grating where the incident angle was swept from −30 to 30 degrees, according to an illustrative aspect of the invention.

FIG. 19 graphically shows simulated photocurrents from four distinct diode arrays at 0, 90, 180, and 270 degrees relative to a grating where the incident angle was swept from −30 to 30 degrees, according to an illustrative aspect of the invention. As can also be seen from FIG. 19, each diode shows multiple peaks, indicating that equations (1) may not necessarily lead to a unique angle extraction. This may be remedied by using multiple structures with different grating geometries (and therefore different values of "k"), placed adjacent to each other. If the mapping from incident angle to diode response is different, then different peaks of activity may be distinguished. This may then facilitate construction of a sensor that is able to cover the entire range of incident angles.

In the ideal case where each diode is responding to exactly the same incident angle of light, one may expect some redundancy in the responses in the eight diode aspect described above. For example, $$D0+D180=D90+D270,$$

implying that maintaining all four separate signals may be redundant. This redundant information may be removed by redefining the response in terms of three numbers:

$$D0-D180,$$

$$D90-D270, \text{ and}$$

$$D0+D180+D90+D270.$$

This recoding could be performed in either the analog or digital domain on the same integrated circuit as the sensors and gratings.

If incident angle is not constant across the imager (as would be the case in FIGS. 1b and 20a-c), then adjacent gratings will not see identical incident angles. Since the four diodes, D0, D90, D180 and D270 are not all interleaved with each other, but appear in adjacent pixels, they may encode slightly different incident angles, and so contain some non-redundant information that would be lost in recoding. Nonetheless, recoding signals can provide benefits by allowing for different weighting of different components of the data before conversion to digital signals or before transmission off chip.

Figure 21:
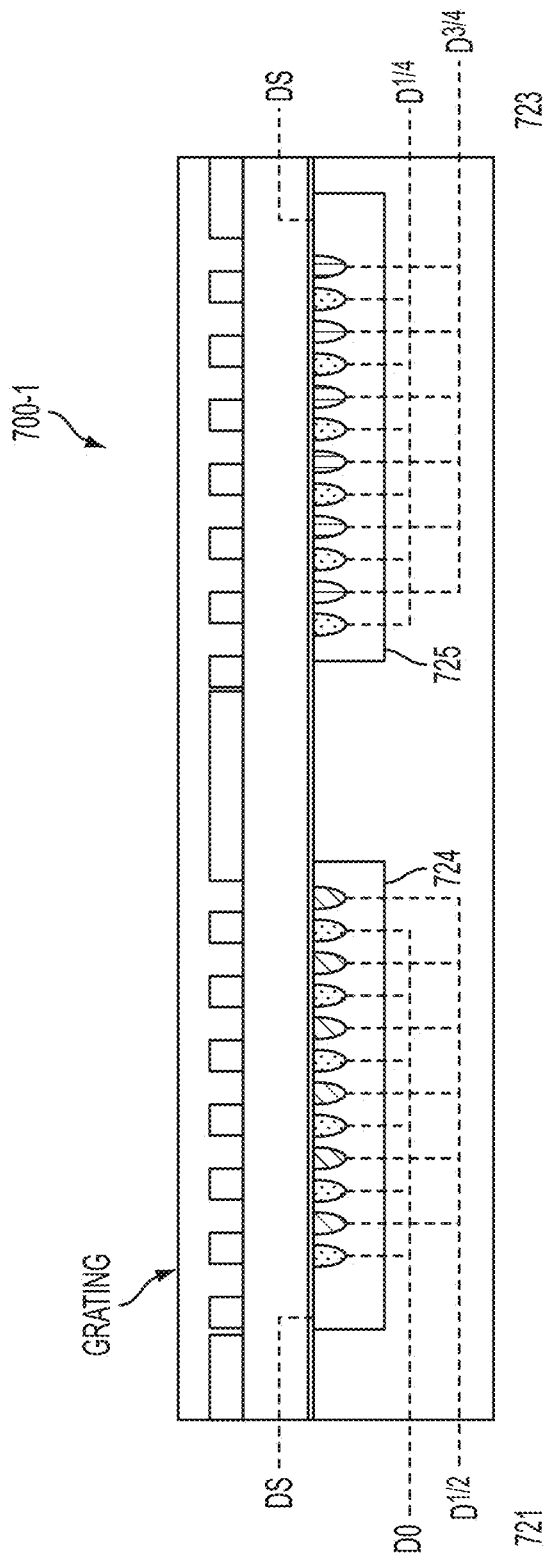
FIG. 21 is a diagrammatic cross sectional view of an image sensor according to an alternative aspect of the invention.

FIG. 21 shows a device embodiment 700-1 similar to that of device 100-1 in FIG. 15, with the exception that the two sets of interleaved diffusion-type diodes 121, 123 (721, 723) are, respectively, disposed in two single, large well-diodes 724, 725. According to this aspect, crosstalk observed in the sub-micron size diffusion-type diodes may be reduced, since the large photodiodes collect the electrons and holes generated by photons that penetrate into the substrate beyond the thin, interleaved diodes. Thus the large well diodes are fabricated deep enough to enclose the interleaved diodes but shallow enough to catch electrons.

Figure 22:
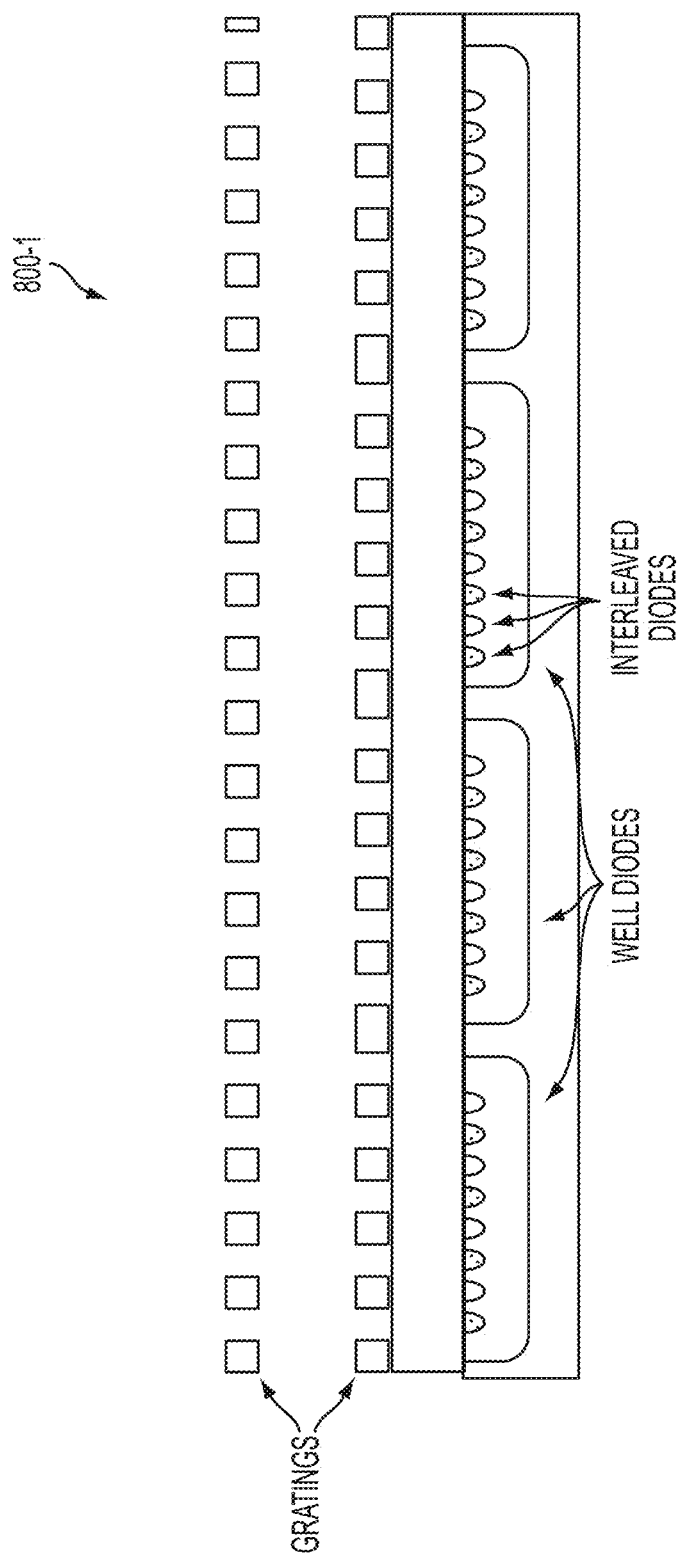
FIG. 22 is a diagrammatic cross sectional view of an image sensor according to an alternative aspect of the invention.

Interleaved/deep-well diodes can also be incorporated into devices which rely on multiple sets of gratings for angle sensitivity. An example device 800-1 using two gratings placed ½ Talbot distance apart vertically and photodiodes at the 1$^{st}$ Talbot distance is shown in FIG. 22. As described above, the large-well photodiodes measure the total light flux passing through the two gratings. In this aspect, the mode of operation is identical to that of the basic multiple grating device. However, when the incident angle is such that the light flux through the grating stack is strong, the interleaved photodiodes help locate the lateral offset of the periodic intensity pattern with greater accuracy. This provides improved characterization of incident angle around a set of known angles without interfering with basic function.

As detailed above, Talbot self-images are used to perform incident angle measurements. Modern semiconductor manufacturing is used to form a micron-scale, fine-pitch transmission amplitude grating that creates interference patterns (Talbot images) from light impinging upon it. Changing the light field incident angle causes these interference patterns to shift laterally, which can be detected by a detector. Characterizing these shifts allows one to determine incident angle at a pixel scale. However, the above disclosed apparatus and method of incident angle measurement using a metalized top grating significantly reduces sensitivity of the detector to local light intensity. The metal gratings used to generate the interference patterns block a significant fraction of the available light. While reduced light sensitivity is not a significant problem for many applications, maintaining high sensitivity comparable to that of a traditional photodetector permits more widespread deployment of angle-sensitive imagers.

According to an embodiment that can mitigate this loss of sensitivity, a micron-scale phase grating formed at a pixel scale in an image sensor chip is used in place of the top, amplitude transmission grating. A phase grating similarly creates an interference pattern and therefore generates Talbot self-images, which we characterize in a manner similar to the embodiments disclosed above. In using phase gratings, we replace the top metal (e.g., wire grid) diffraction grating with a three-dimensional structure (i.e., phase grating) containing materials possessing a different refractive index from that of the sensor chip substrate. This provides significantly increased light sensitivity as there are no wires to block light striking the pixel.

Figure 23A:
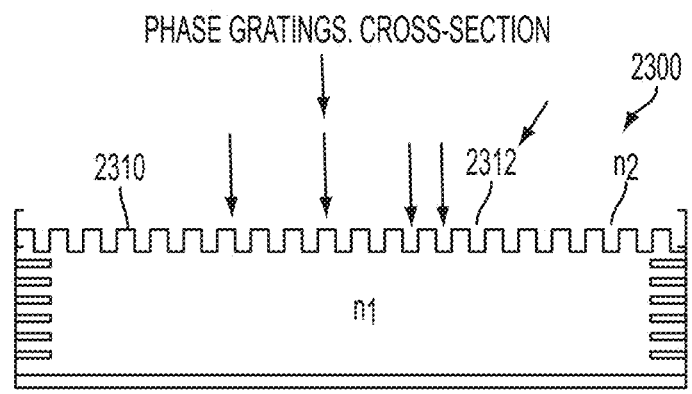
FIGS. 23(a-d) illustrate a phase grating based ASP and simulated Talbot images according to an exemplary embodiment of the invention.
Figure 23B:
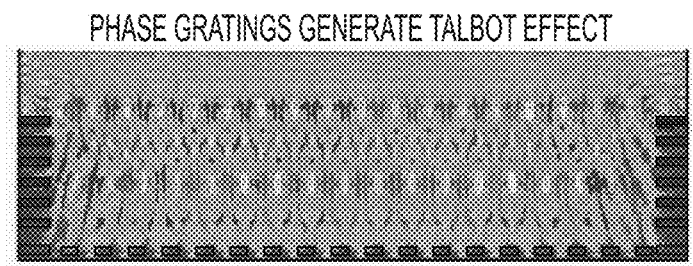
Figure 23C:
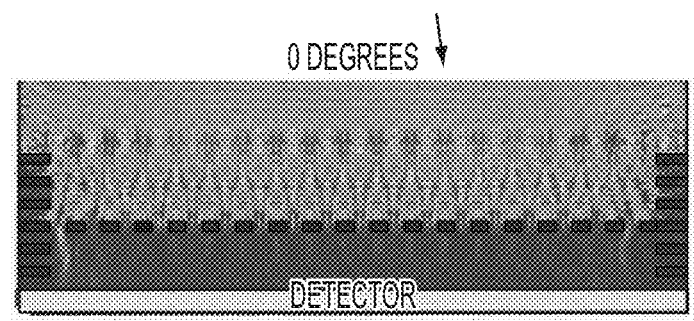
Figure 23D:
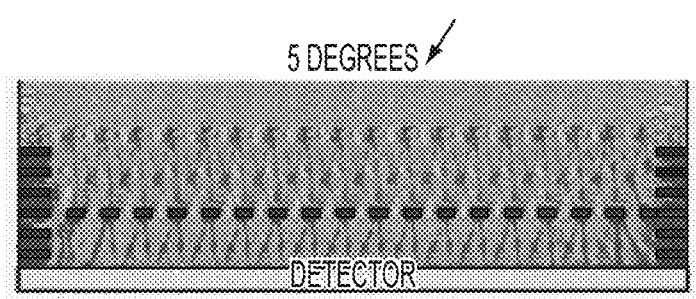

A simple phase grating 2300 can be formed using crenellated structures such as those shown in FIG. 23a. The shaded area 2310 is a material of refractive index $n_1$, while the white area 2312 is a material of refractive index $n_2$. Incident wavefronts (arrow) which pass through the peaks of the crenellations exhibit a phase shift relative to those which pass through the valleys. By Huygens' Principle, the phase shift differences and the path length differences predict periodic intensity patterns similar to those observed with transmission amplitude gratings (FIG. 23b). The location of these patterns is influenced by the illumination wavelength and (phase) grating pitch. As shown in FIGS. 23c, d, the intensity patterns shift laterally as the incident angle of illuminating light changes.

As disclosed above, information about the angle of incident light can be extracted from the lateral shifts in the diffraction pattern. However, the analyzer grating of a single ASP samples only one phase of the periodic intensity pattern; thus the output of a single angle-sensitive pixel cannot distinguish between changes in intensity and incident angle. The differential signal from a pair of ASPs whose phases (α's) differ by π is required to unambiguously recover angle information. Exemplary angle sensitive pixel arrays disclosed hereinabove used four ASPs, where each ASP's response has identical m and fi parameters but distinct values for α (α=0, π/2, π, 3π/2) to obtain a full quadrature description of incident angle.

However, since several ASPs are required to completely characterize angle, angle information is captured at a significantly reduced spatial resolution as compared to intensity information. In the above disclosed embodiments, the metal gratings used to achieve angle sensitivity block a significant fraction of incident light from the photodiode. As a result, the quantum efficiency (QE) of the above embodied ASP devices is 6-10 times less than an equivalent, exposed photodiode without gratings. This reduced sensitivity limits the usefulness of angle-sensitive pixels in low-light and high speed imaging applications.

Figure 24B:
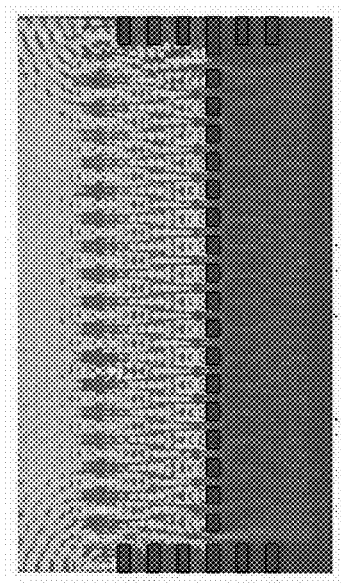
FIG. 24b shows simulated Talbot images at normal incidence.
Figure 24D:
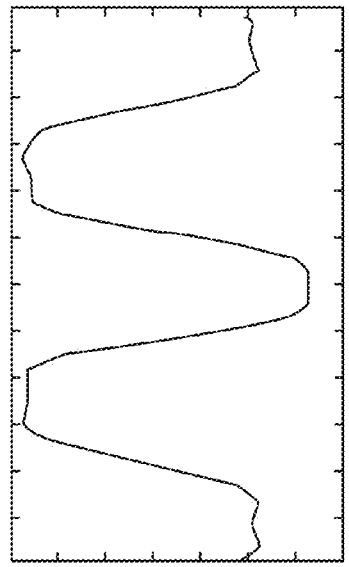
FIG. 24d shows a measured response of the detector as a function of incident angle, according to an exemplary embodiment of the invention.
Figure 24A:
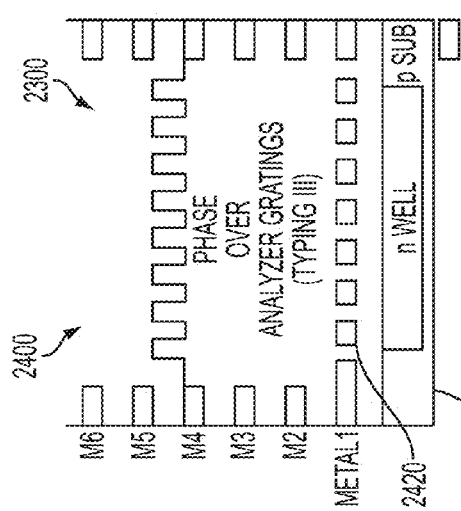
FIG. 24a is a phase grating based ASP with an analyzer grating.
Figure 24C:
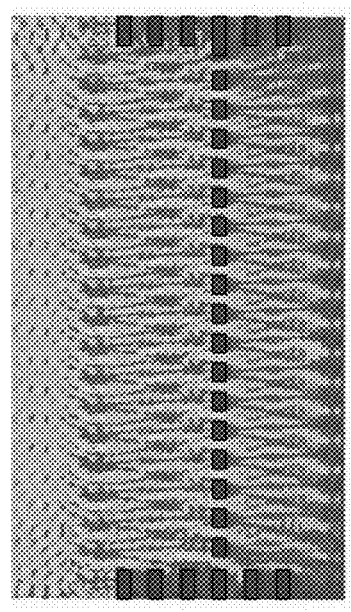
FIG. 24c shows simulated Talbot images at 10 degrees.

FIG. 24a illustrates one exemplary ASP device 2400 and technique, with a periodic, rectangular binary phase structure 2300 implemented in an intermetal dielectric layer stack, and an amplitude grating 2420 positioned below (i.e., optically downstream) the phase grating 2300 in the plane where strong intensity (Talbot) patterns are created by the phase grating. As the intensity patterns shift due to changing incident light angle, they align with either the bars or the gaps of the amplitude grating 2420. When intensity peaks align with the bars as shown in FIG. 24b, most of the light is blocked and a detector 2430 located below the analyzer grating registers a weak response. When peaks align with the gaps as shown in FIG. 24c, most of the light passes through to the detector below. This produces the alternating strong and weak response shown in FIG. 24d.

Figure 25A:
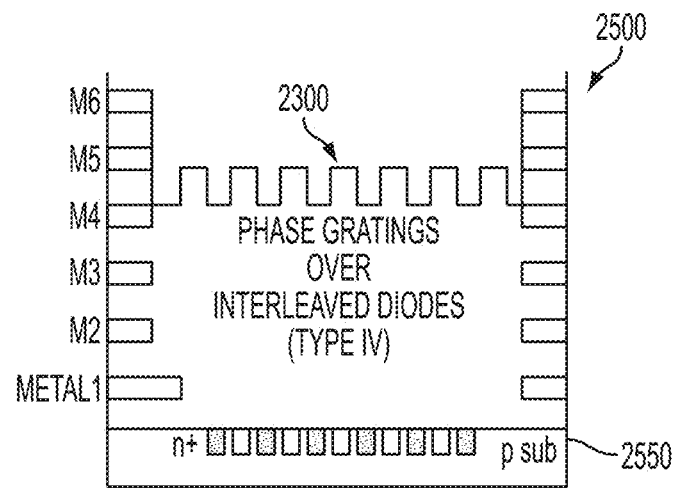
FIG. 25a is a cross sectional view of a phase grating based ASP with interleaved finger diodes.
Figure 25B:
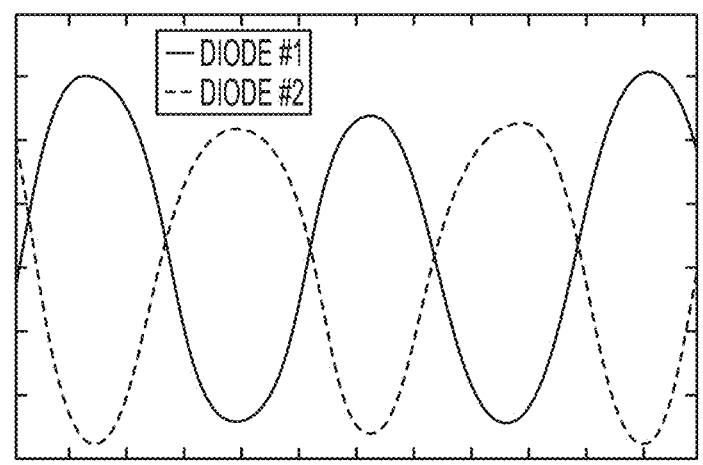
FIG. 25b shows a measured response of the detector as a function of incident angle, according to an exemplary embodiment of the invention.
Figure 26A:
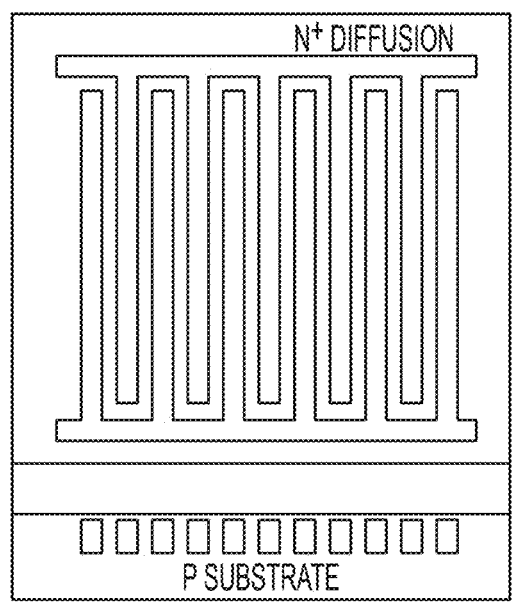
FIG. 26a is a top cross sectional view of a pair of interleaved diodes.
Figure 26B:
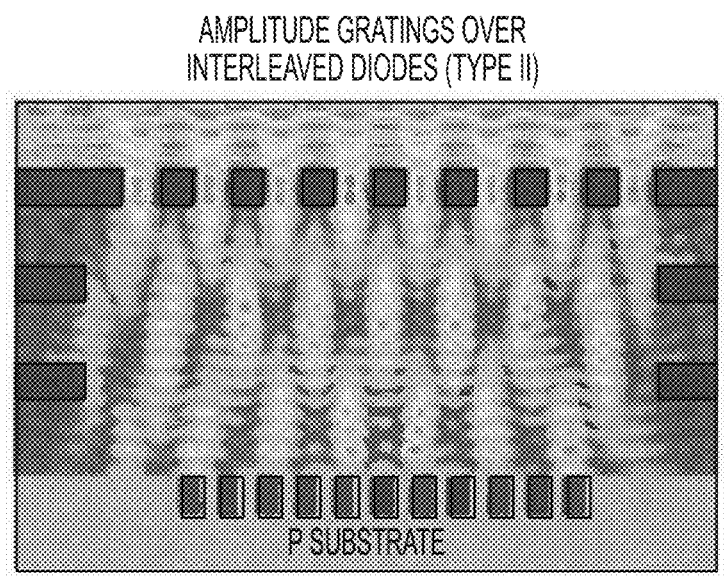
FIG. 26b shows an ASP that uses interleaved diodes instead of an analyzer grating and an n-well diode to detect complementary phases of a single diffraction pattern, according to an illustrative embodiment of the invention.

FIG. 25a illustrates another embodiment of the invention. The ASP device 2500 includes the phase grating 2300 as illustrated in FIG. 24a. In this embodiment, however, there is no analyzer grating; rather, an interleaved collection (e.g., a pair) of small detectors 2550 are located in the plane containing the strong intensity (Talbot) patterns produced by incident light interacting with the phase grating. These detectors directly measure the patterns as they shift in response to incident angle. Intensity maxima on the detectors result in strong response, while intensity minima result in weak response, as illustrated in FIG. 25b. More specifically, the detectors 2550 are a pair of interleaved N+/p-substrate diffusion diodes. The outputs of this diode pair record complementary phases of the Talbot pattern. This structure, therefore, enables the direct capture of angle information while eliminating the lower metal (analyzer) grating as shown in FIG. 24a. FIGS. 26a, b show a schematic structure of an ASP that uses a pair of interleaved N+/p-substrate diffusion diodes and a Finite-Difference Time-Domain (FDTD) simulation of the capture of the complementary phases of a single diffraction pattern.

The effects of grating pitch, height, and index mismatch on the depth, strength, and angle sensitivity of resulting Talbot patterns all influence the Talbot effect for phase gratings at the scale of only a few wavelengths.

One of the major benefits of the parent invention amplitude-grating based ASPs is that they can be made in completely standard CMOS with no post-processing. This has a variety of benefits, such as low cost and ease of manufacture. Unfortunately, a standard CMOS layer stack provides no ready-made components for phase gratings similar to the wires used for amplitude gratings.

Techniques from CMOS MEMS (see, e.g., Fedder, Santhanam et al. 1996; Fedder 1997) can be employed to build phase gratings by using metal structures as etch stops for anisotropic oxide etches. Using the available metal layers permits for high-precision phase grating fabrication without additional masks or patterned depositions. A summary of the process is illustrated in FIG. 27 for both interleaved diode ASPs (bottom) and analyzer grating ASPs (top). FIG. 27a illustrates the cross section of a chip as manufactured, in which top two metal layers (black) have been used as etchstop layers. Starting with a standard CMOS stack of patterned metal embedded in silicon dioxide, we then use a deep reactive ion etch (DRIE) to remove silicon dioxide, stopping on the metal layers, as in FIG. 27b. This oxide etch is followed with a metal etch, which leaves a patterned interface between the oxide and adjacent material (e.g., air, unless subsequent layers are added; FIG. 27c). By appropriately designing the metal etch stops that define the tops and bottoms of the phased gratings, we can control the pitch and alignment of the gratings. Choosing which pairs of metal layers to use provides some control of grating height.

An alternate approach that yields a similar result is to use only one grating as an etch stop (to define the high parts of the phase-grating crenellation), and use a timed oxide DRIE to etch out the low parts of the phase grating. Once again, this is followed with a metal etch to expose the high parts and generate a pure phase grating.

This basic post-processing requires only a few steps and no precision alignment, so the additional cost beyond that of the manufactured chip will be low. Additional steps may be advantageous, such as a bulk etch removing chemically distinct passivation layers. Protecting the input/output pads of the chip may also require a coarse alignment step and a low-resolution mask. Nevertheless, using the CMOS stack as a substrate for phase grating fabrication significantly simplifies manufacturing.

Alternatively, other methods of generating phased gratings can be employed, such as nano-imprint lithography, or direct patterning using periodic masks and standard photolithography.

The relative refractive index at the grating interface can be modified (from the 1:1.4 of air and $SiO_2$) with a conformal coat of additional material, as illustrated in FIG. 27d; for example, adding parylene would provide a 1.66:1.4 interface and provide protection from water. Altering the change in refractive index provides further control over the precise location of the self-images beyond that available through grating pitch and height. Preliminary simulations indicate that the heights (~1 μm) available in standard CMOS, and available interface indices (air, parylene) should provide reasonable performance. In addition, deliberately choosing a dispersive material will make it possible to generate wavelength-independent phase shifts, reducing the sensitivity of the Talbot effect to wavelength.

As disclosed hereinabove, another source of reduced sensitivity is the analyzer grating. Regardless of the (top) grating used to generate the Talbot self-images (amplitude or phase grating), the (bottom) analyzer grating will still block light that is out of alignment. However, if the lateral shift of the Talbot self-images is directly detected by photodiodes, the analyzer grating is no longer necessary.

Figure 28A:
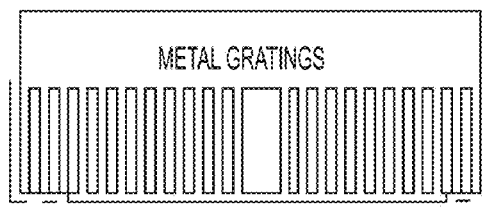
FIG. 28a schematically illustrates a top view of the metal gratings of an ASP; top views of grating, diodes (dark/light regions indicate different offsets)
Figure 28B:
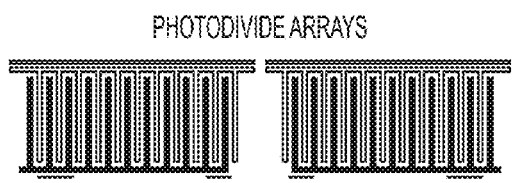
FIG. 28b schematically illustrates a top cross sectional view of an ASP using interleaved "fingered diodes" (dark/light regions indicate different offsets) directly in place of analyzer grating.
Figure 28C:
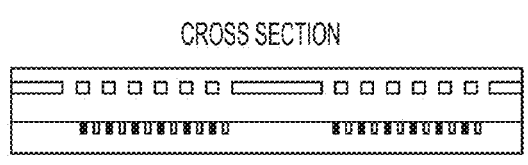
FIG. 28c schematically shows the ASP in cross section.

One simple approach for accomplishing this is illustrated in FIGS. 28a-c. By interleaving two distinct sets of photodiodes, one can detect whether the self-image is in phase or precisely out-of phase with the primary grating. Using a second set of such interleaved photodiodes at a ¼ pitch offset results in a set of outputs analogous to those shown in FIG. 5 for stacked amplitude gratings. Ideally this would provide better quantum efficiency while requiring half as much area for a given ASP, since two measurements would result from each structure.

Figure 28D:
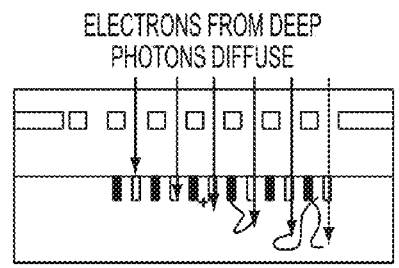
FIG. 28d is a schematic illustration of how shallowly penetrating photons (arrows) generate photocurrent in desired diodes but electrons from deeply penetrating photons can diffuse to either set of fingered diodes blurring angle sensitivity.
Figure 28E:
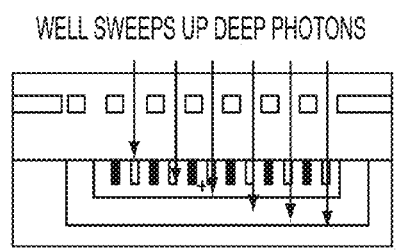
FIG. 28e schematically illustrates how embedding interleaved diodes in a well causes deeper photons to be absorbed in or near the well's depletion regions preventing blurring while still detecting all photons for intensity measures.
Figure 28F:
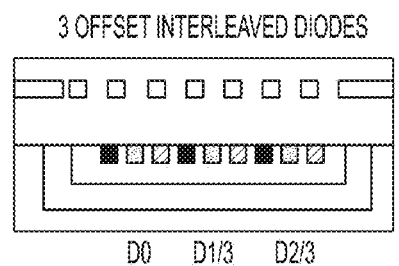
FIG. 28f schematically illustrates an alternate interleaved diode design with three wider diodes to capture three angles, according to an illustrative embodiment of the invention.

This approach requires very fine resolution photodiodes on the scale of 0.5 μm pitch. FIG. 28 illustrates a phase grating-based ASP using interleaved "fingered diodes" in place of an analyzer grating. FIGS. 28a, b are top views of the grating and diodes, where the different colors indicate different offsets. FIG. 28c shows the ASP device in cross section. FIG. 28d illustrates how shallowly penetrating photons (green arrows) generate photocurrent in desired diodes (red) but electrons from deeply penetrating photons can diffuse to either set of fingered diodes (red or blue), blurring angle sensitivity. FIG. 28e illustrates how embedding interleaved diodes in a well causes deeper photons to be absorbed in or near the well's depletion regions, (violet) preventing blurring while still detecting all photons for intensity measures. FIG. 28f shows an alternate interleaved design with three wider diodes to capture three angles.

Such diodes can be made using the source/drain diffusions of a CMOS process, which are typically very shallow. Since these depths (also <0.5 μm) are significantly shallower than the penetration depth of visible light, much of the light will be absorbed at depths greater than that of the photodiodes themselves. This implies both a reduced quantum efficiency as some photo-generated carriers diffuse away or recombine and, that many (likely the majority) of the photo-generated carriers will diffuse at least 0.5 μm before being absorbed by a photodiode. As a result, photons absorbed below the photodiodes will generate carriers with a roughly equal chance of being absorbed by either photodiode, badly blurring their ability to detect shifts in the Talbot pattern (see FIG. 28d). This is a known problem with fine pitch photojunctions, and has limited resolution in other high-resolution imaging systems.

To avoid this penetration/diffusion problem, the interleaved, "fingered diodes" can be placed in a deeper, more lightly doped well. These wells are available in most modern CMOS processes with both n- and p-doping (FIG. 28e). By providing a shallow boundary to the silicon below the fingered photodiodes, this well would absorb most of the carriers generated by deeply penetrating photons, reducing blurring. By measuring the current generated by these deep photons overall intensity could be measured with high quantum efficiency, even as the interleaved diodes extract incident angle information. Simple simulations indicate that for a reasonable CMOS process (at the 130 nm or 180 nm process node), approximately 30% of green light would contribute to angle-sensitive photocurrents, providing similar modulation depth when compared to stacked amplitude gratings. The remaining light would provide additional intensity information. The ratio of well current to total finger current in such a structure would also provide information about the wavelength of the light detected since the average penetration depth of a photon depends upon its wavelength.

A second challenge with interleaved diodes is that the pitch they require is very close to the limit of what is possible in reasonably priced (i.e., 180 nm) CMOS. One approach to reduce this problem while further increasing density is shown in FIG. 28f. Simulations show that three distinct sets of fingered diodes, at a pitch of ⅔ the grating pitch, extract three periodic, angle sensitive signals split by 120 degrees (as compared to the 90 degree splits described hereinabove for the stacked amplitude grating ASPs). These three independent measurements are sufficient to extract everything about a simple Talbot self-image. Specifically, these three numbers map, after transformation to the total light intensity, modulation depth of the self image (reflects how "blurry" the incident angle is), and the angle itself. Thus such a structure can provide extremely dense ASPs.

Both phase gratings and interleaved photodiodes can be independently deployed as improvements to stacked grating ASPs. The greatest benefit will result when combining these approaches to produce a sensor structure with an overall quantum efficiency and density equivalent to a typical angle insensitive pixel while simultaneously capturing additional information about the light field.

The accuracy of an ASP array in localizing light sources in 3D space is inversely proportional to the angular gain of an ASP. This gain is proportional to z/d, where d is the grating pitch and z is the vertical separation between grating and analyzer structure. All of these structures have made use of the ½ Talbot depth, where, at the optimal $z=d^2/\lambda$, the angular gain is simply $d/\lambda$ and is limited by the available layer stack, metal dimensions, and requirement that $d>\lambda$ (required to observe the Talbot effect). However, one is not confined to using the ½ Talbot depth. Simulations show that the Talbot effect produces self-images at a variety of depths beyond the ½ Talbot depth. As the lateral shift of the Talbot effect is $\Delta x=z \tan(\alpha)$, increasing z by choosing a deeper Talbot self-image results in a greater lateral shift for a given incident angle, and therefore greater angular gain.

An alternative approach to achieving greater angular gain would be to use a higher periodicity self-image. For example, the phase grating simulation of FIG. 23 shows Talbot patterns with higher (particularly, double) periodicity than the generating grating at depths above and below the ½ Talbot depth. If we place interleaved diodes or analyzer gratings at the depth and with the same pitch as these fractional patterns, the same lateral shift will correspond with a stronger change in response. This also corresponds to higher angular gain.

Figure 29A:
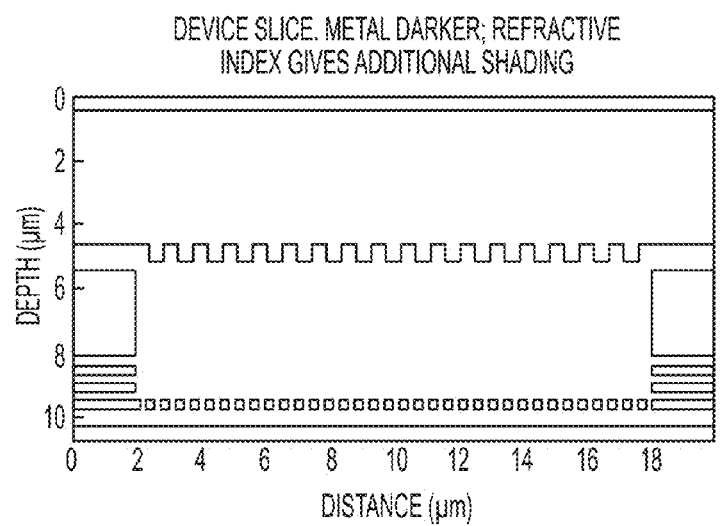
FIG. 29a: Quarter-order Talbot phase gratings where the pitch of the diffractive layer is twice that of the analyzer layer.
Figure 29B:
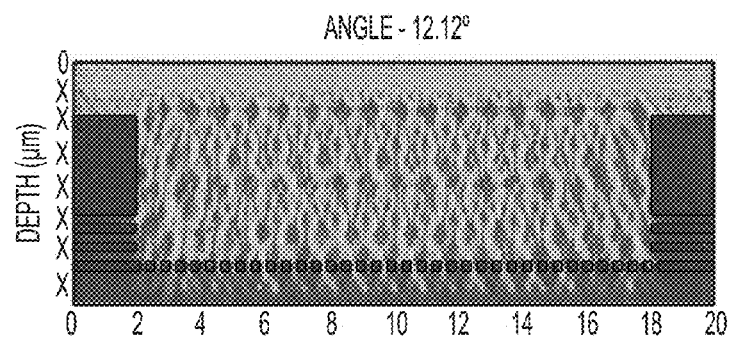
FIG. 29b: Quarter-order Talbot phase grating simulation of light interacting with the device.
Figure 29C:
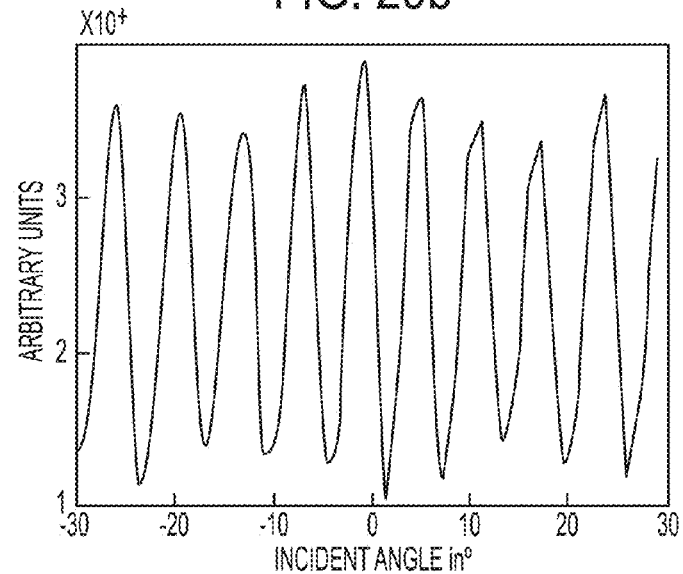
FIG. 29c: Quarter-order Talbot phase gratings showing angle sensitivity of quarter-order Talbot device, according to an illustrative embodiment of the invention.

For a fixed depth between the initial grating and the sensor or analyzer grating, the pitch of a phase grating will be twice that of an analyzer grating. Therefore the default angular sensitivity (b) of phase gratings (computed by b=depth divided by pitch times 2n) would be half that of similar amplitude gratings, barring further intervention. However, it is possible to exploit higher-order Talbot patterns such as the ¼ order patterns, as shown in FIG. 29. FIG. 29*a* shows a cross section of a device engineered to use the 10¼ order Talbot depth, where the period of intensity is twice the pitch at the diffractive layer. FIG. 29*b* shows that there are many higher-order Talbot depths available; all depths with higher spatial periodicity than the phase grating will exhibit high-order Talbot patterns (and thus greater angular sensitivity). FIG. 29*c* shows the simulated angular sensitivity of this device; it has a b of 66.

Figure 30:
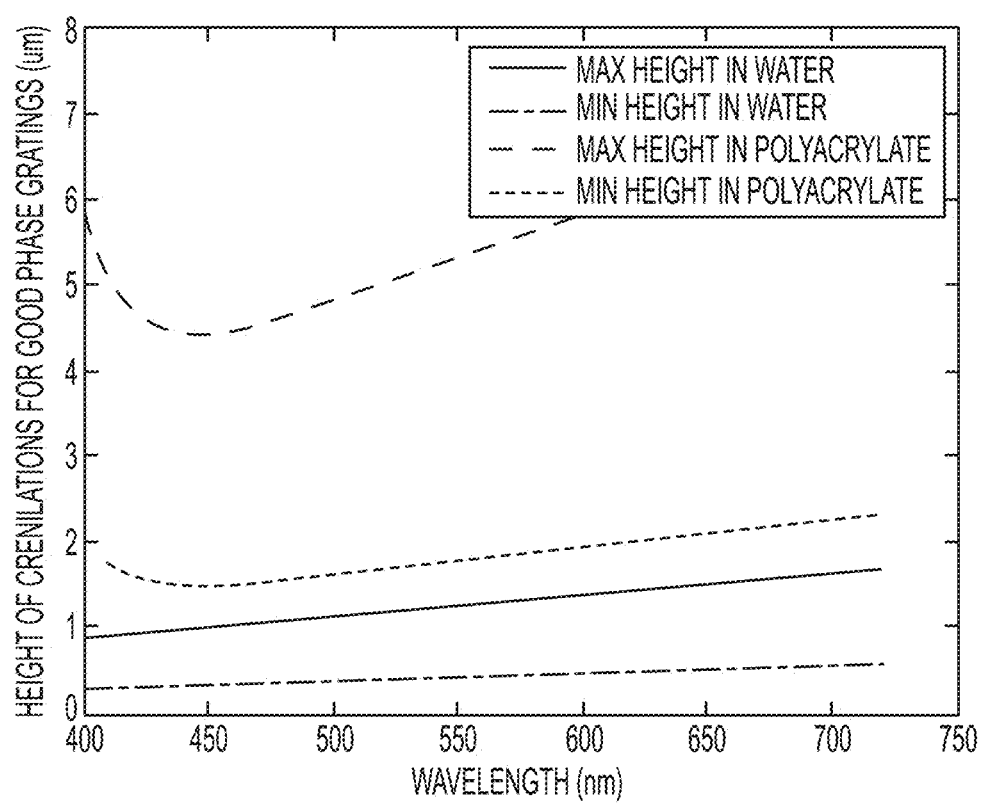
FIG. 30: Graph showing the effect of a dispersive medium in the phase grating.
Figure 31B:
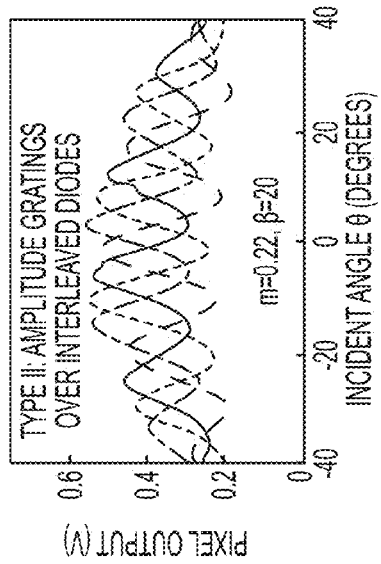
FIG. 31b: Measured output of four ASP structures showing all ASP structures achieve a characteristic angle sensitive output response, according to a illustrative aspect of the invention.
Figure 31D:
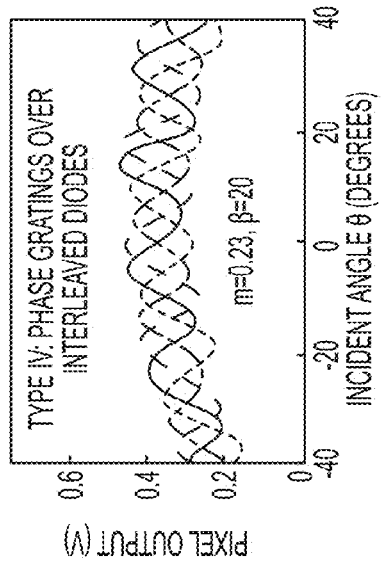
FIG. 31d: Measured output of four ASP structures showing all ASP structures achieve a characteristic angle sensitive output response, according to a illustrative aspect of the invention.
Figure 31A:
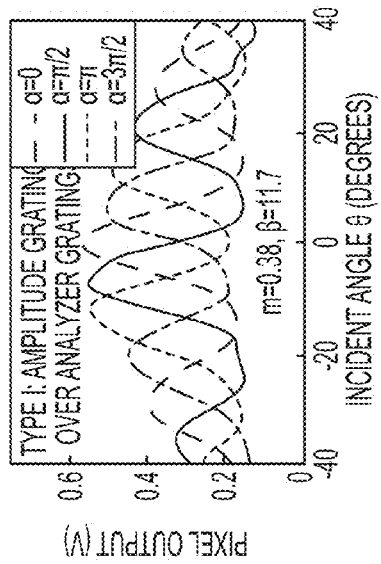
FIG. 31a: Measured output of four ASP structures showing all ASP structures achieve a characteristic angle sensitive output response, according to a illustrative aspect of the invention.
Figure 31C:
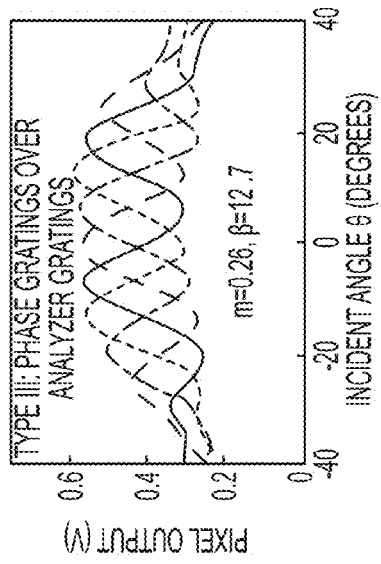
FIG. 31c: Measured output of four ASP structures showing all ASP structures achieve a characteristic angle sensitive output response, according to a illustrative aspect of the invention.

Since phase gratings are used to induce a phase shift, whereas materials of different indices of refraction contribute to different optical path lengths, one would assume that the depth of phase gratings should be proportional to the wavelength in use. When polychromatic light is observed, the depths of the phase gratings will not be tuned appropriately for all wavelengths without intervention. It is possible to mitigate this effect by using a dispersive substance such that over some range of wavelengths the difference in refractive indices of $SiO_2$ and the superstrate are somewhat proportional to wavelength. For example, if a plastic with similar optical dispersion to polyacrylate were patterned on top of the $SiO_2$, the ideal grating thickness becomes less sensitive to wavelength. As shown in FIG. 30, with a water coating, the range of appropriate phase grating heights is roughly proportional to wavelength. With a dispersive medium (such as a polyacrylate layer), some of the wavelength dependence can be mitigated since the refractive indices of the media composing the gratings are closer at lower wavelengths than at high wavelengths.

Four variants of ASPs have been experimentally characterized and are listed in Table I.

TABLE I

FABRICATED ANGLE SENSITIVE PIXEL STRUCTURES

| ASP type | Top Grating | Analyzer grating | Photodiode type | Signals/pixel |
|---|---|---|---|---|
| I | Amplitude | Amplitude | N-well/p-substrate | 1 |
| II | Amplitude | None | Interleaved n+/p-substrate | 2 |
| III | Phase | Amplitude | N-well/p-substrate | 1 |
| IV | Phase | None | Interleaved n+/p-substrate | 2 |

The angular response of the ASPs were measured under green (523 nm, spectral half width 20 nm) plane wave illumination over an 80° range of incident angles. FIGS. 31*a-d* show the measured four phase output for each of the four ASP types. All four ASP structures trace the desired quadrature angle response. In the case of ASPs with interleaved photodiodes, complementary phase responses were measured from a single 8 µm×8 µm pixel. Newer ASP designs, types II, III and IV, exhibit modulation depths in the range 0.2-0.3 as compared to amplitude grating ASPs with peak modulation depths above 0.4. For interleaved diode based ASPs, this degradation could be due to stray carriers from the substrate regions between and below the interleaved diodes. Deviations from the ideal phase step of π/2 likely result in poorer modulation of intensity patterns generated by the phase gratings. Further characterization is required to establish the effect of variations in the grating step.

Figure 32:
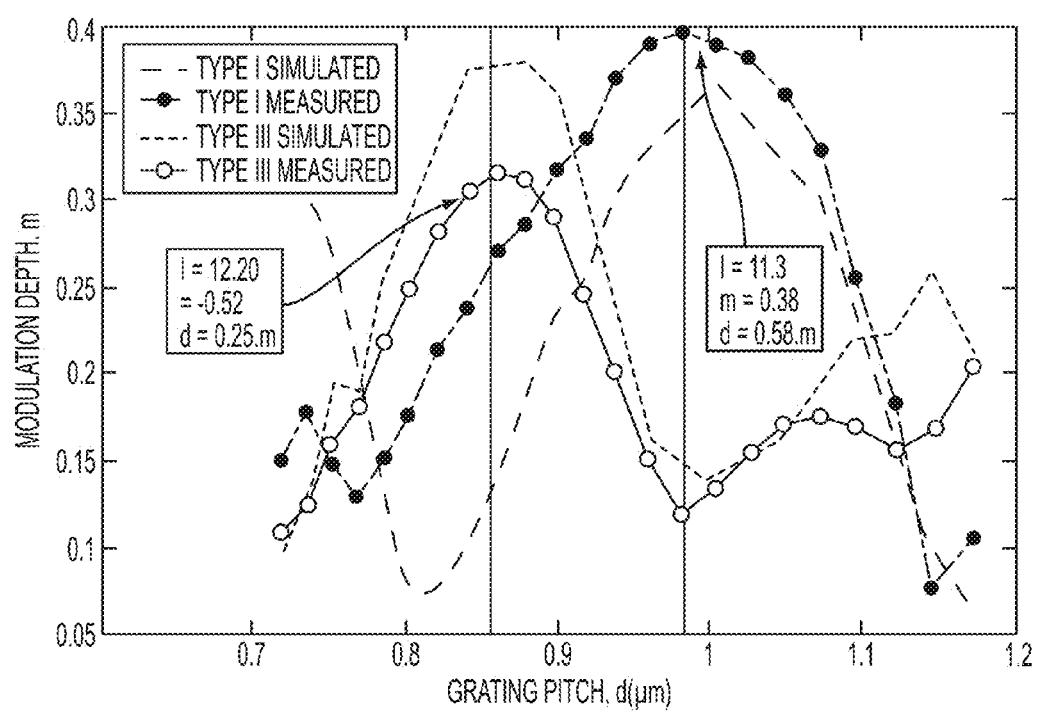
FIG. 32: Graph showing the measured variation of modulation depth and angular sensitivity with grating pitch. The highest modulation depth of m=0.32 is obtained when grating pitch, d=0.86 µm.

For each ASP structure, the dependence of output on grating pitch and position was characterized. Measurements were made for ASPs with grating pitch, d, ranging from 0.6 µm to 3.2 µm and four different vertical grating separations allowed by the CMOS metal stack. The measured and simulated variation of modulation depth, m, with grating pitch is shown in FIG. 32 for an amplitude grating (type I) ASP with analyzer grating depth, z=2.76 µm and a phase grating ASP (type III) with analyzer grating depth, z=2.33 µm. For a desired angular sensitivity of 12, we predict a grating pitch, d=1.03 µm for the type I ASP and d=0.87 µm for the type III ASP. These calculations are consistent with measured results.

Figure 33:
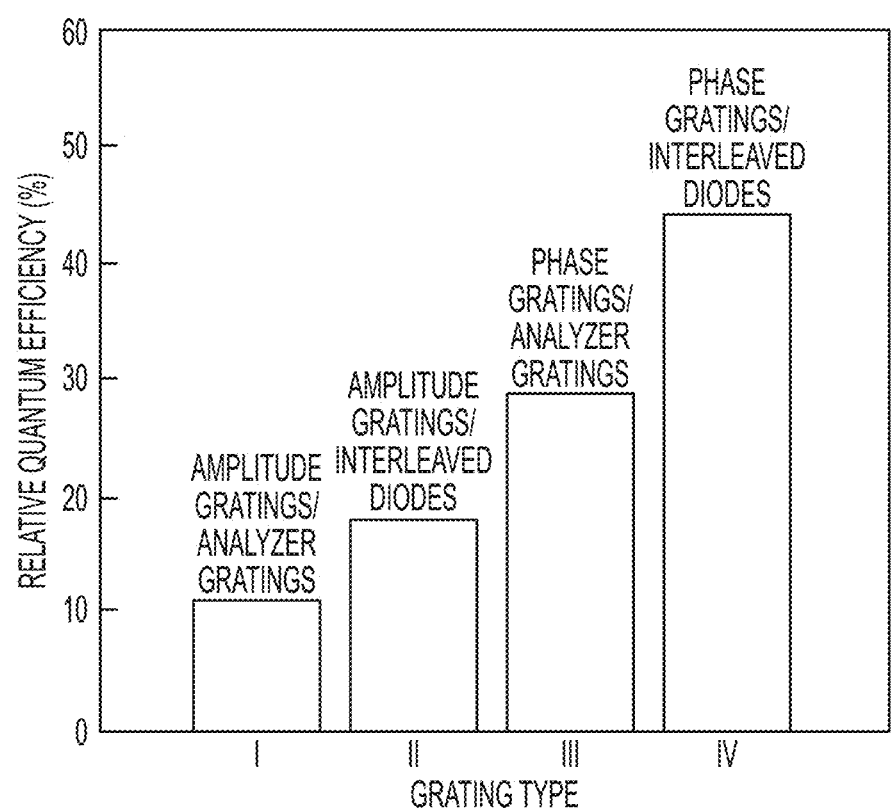
FIG. 33: Chart showing the measured quantum efficiency of four ASP variants, relative to a conventional active CMOS pixel with an n-well/p-substrate photodiode.

The QE of all the ASPs were measured and normalized to an n-well-p-substrate diode without gratings. The measured quantum efficiency of the four variants of ASPs shown in FIG. 33 confirms that the efficiency loss caused by metal gratings can be recovered by a combination of phase gratings and interleaved diodes.

For many applications, temporal information of incident light as well as spatial and angular information is important. One example is LIDAR, in which the time delay between light pulse emission and reflected pulse detection provides a measure of distance. Fluorescence imaging can also benefit from temporal information, which provides a means to discriminate between stimulation photons and fluorescence photons without complex filter optics. Combining angle sensitivity with very high frame rates (upwards of 100M frames/s) allows for these and other applications to take advantage of the additional information contained in incident angle.

Existing research has shown that stand-alone CMOS chips can perform this class of high speed temporal imaging. Since the ASP can be manufactured in a standard CMOS process, and since angle sensitive behavior relies on purely optical phenomena, we believe high speed CMOS imaging techniques can be integrated into angle-sensitive pixels. For example, high speed devices, such as single-photon avalanche diodes and advanced detectors designed specifically for time resolved imaging as methods, may be employed to achieve this integration. These time-resolved ASPs will greatly enhance existing high speed image sensors.

Current research is aimed toward small arrays of ASPs which are capable of performing bioassays without a microscope. However, for real-world imaging applications, small arrays are incapable of capturing the full complexity of observed scenes. Large array of at least 200,000 ASPs may allow for real-world imaging applications of our enhanced ASPs. This high resolution will demonstrate the compatibility of ASPs with traditional imaging applications, and provides a platform which demonstrates the richness of information gathered by an ASP array in comparison to a pure intensity imager.

To achieve the required density within a small, low cost chip, various methods for ASP miniaturization can be employed. For example, current ASPs have distinct, local gratings for each diffraction grating/analyzer grating stack. These finite gratings exhibit edge effects which degrade the Talbot self images and therefore require a minimum number of repeated periods for robust function. Initial simulations have shown that different sensors can share the Talbot self images generated by a single, shared grating without compromising performance. This should permit drastic grating size reduction, since the required large grating is now amortized among several smaller sensors. Combined with alternative detector circuits which reduce the space required for reading out measured data and interleaved diodes, we believe that the size of existing ASPs can be reduced by an order of magnitude. This will result in low-cost, high-resolution light field sensors which will find wide application.

Another embodiment of the invention is directed to a method for extracting incident light-angle information from a light source object. The ability to detect said angle information has applications pertaining, but not limited to sensor networks and sensor arrays; direction and/or speed of motion detection of objects passing over a sensor such as, for example, the direction and speed of a vehicle passing over a sensor embedded in road pavement; detection/reception of multiple data streams from separate transmitters in a free-space optical communication system; bio-medical applications such as, e.g., detection of individual fluorescent cells in tissue containing such fluorescent cells, and others that would be appreciated by persons skilled in the art.

Figure 1A:
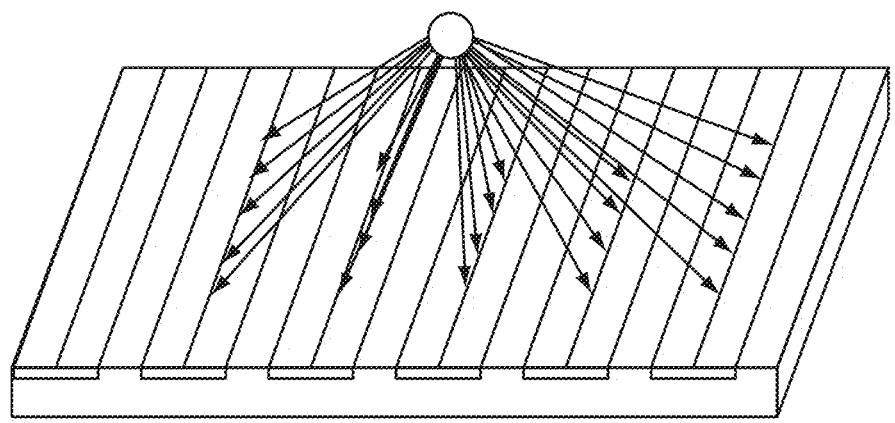
FIG. 1a shows a perspective illustration of a light-field imager and how light from a source strikes each pixel of an array with a distinct incident angle.
Figure 1B:
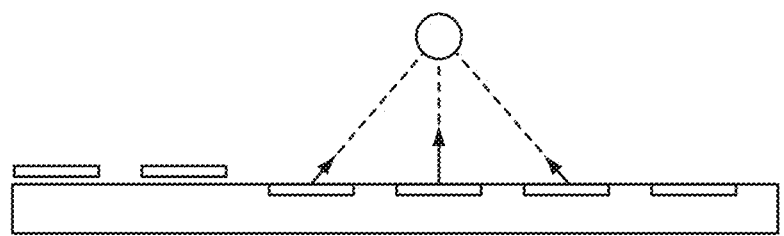
FIG. 1b illustrates that if each pixel in an array can determine the incident angle as well as the intensity of the light it detects, then array is able to localize a light source in three dimensions, according to an illustrative embodiment of the invention.

According to a non-limiting aspect, the method may be accomplished entirely without the use of lenses, and performed with image sensors on the physical scale of silicon integrated circuits. For example, a sensor array as described herein above may be positioned adjacent a piece of tissue containing fluorescent cells. Each cell would generate light whose incident angles (into the sensor) would indicate the cell's location in three-dimensional space. By triangulating back from the angles detected by each sensor in the array, as schematically illustrated in FIG. 1b, the location of individual fluorescent cells could be detected, as well as changes in their fluorescence independently from the other fluorescent cells.

According to a non-limiting aspect, many image sensor arrays could be deployed as part of a larger array of tissue culture chambers. Each individual image sensor would provide monitoring of its respective sample, providing high-throughput analysis of many samples at once.

Figure 20:
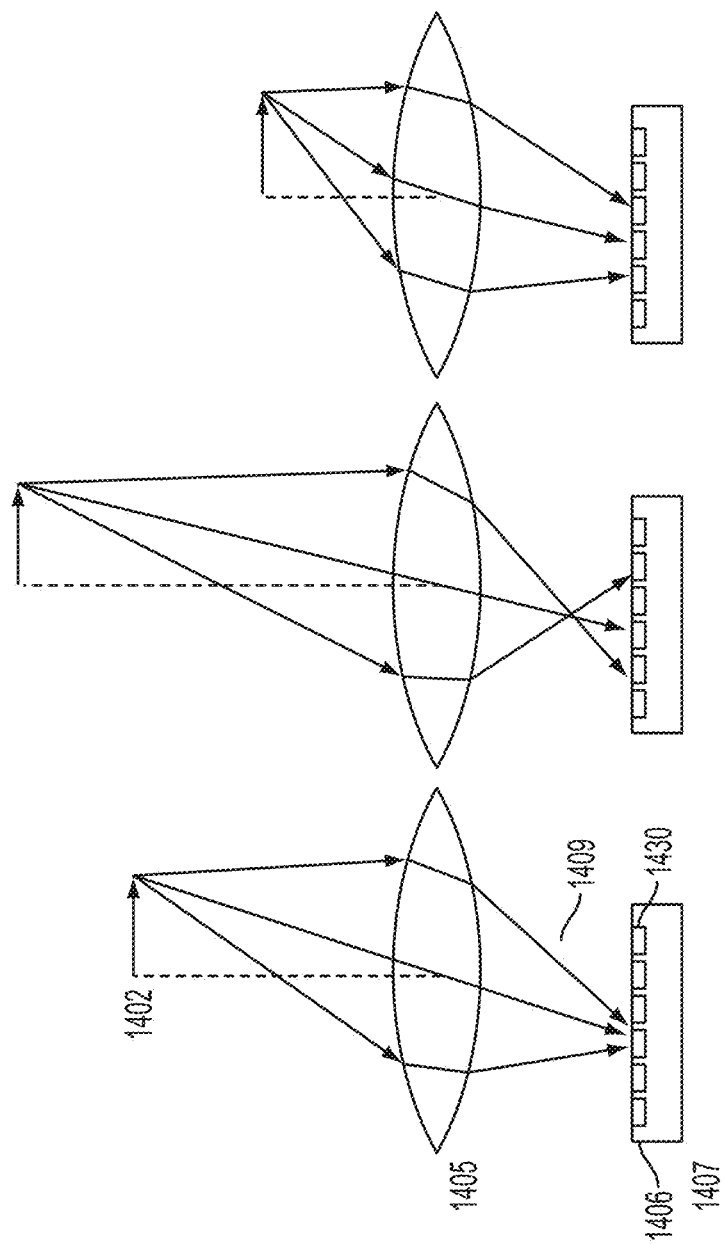
FIG. 20a schematically illustrates the use of incident angle data to compute 3-D locations in conjunction with a lens system, according to an exemplary embodiment of the invention.
FIG. 20b schematically illustrates the use of incident angle data to compute 3-D locations in conjunction with a lens system, according to an exemplary embodiment of the invention.
FIG. 20c schematically illustrates the use of incident angle data to compute 3-D locations in conjunction with a lens system, according to an exemplary embodiment of the invention.

According to a non-limiting, alternative aspect, the method may be accomplished using an imaging sensor in combination with a lens system, which may be advantageous to image more distant objects. For example, as shown in FIG. 20a, an object 1402 at the focal plane of the lens system 1405 will appear completely in focus on the surface 1406 of the sensor array 1407, and will appear to have an even distribution of angles of incidence 1409. In this case the array acts like a normal CMOS imager. Objects more distant than the focal plane of the lens system will generate blurred images on the array, but the blurring will show a variable set of incident angles that converge on the focal plane of the object, as shown in FIG. 20b. Objects closer than the focal depth of the lens system will also appear blurred, but with a divergent set of incident angles, indicating a focal depth behind the array, as shown in FIG. 20c. Thus the imager can extract useful information that can be used to describe the location of objects both closer and farther away than the optical focal plane of the lens system. In other words, the imager, by detecting incident angle, can extract information about an object region that is thicker than the normal depth of focus associated with a given lens system. Thus this information may be used, e.g., to reconstruct the three-dimensional structure of a scene or, to computationally refocus the image to different focal depths after the image has been captured. The data from such an imager may be used to simultaneously refocus different parts of the image to different depths. And although a single light-emitting object will generate a sensor response that maps to a single incident angle, multiple light sources will result in a linear superposition of responses, each of which depends on the incident angle of each source.

Since the diffraction grating approach to light field imaging described herein is sensitive to the wavelength of light, a given pixel design will work effectively for a limited range of wavelengths. For applications where this wavelength is known in advance, such as in fluorescent microscopy or communication systems using known LEDs, the gratings can be designed appropriately as known in the art. In imaging and/or angle detection applications using white light, a color filter 1430 may be required in conjunction with the chip to limit the incident light wavelengths to the appropriate range. Modern imager processes typically include such color filters; thus they could be incorporated into the basic design. Furthermore, since such processes typically include multiple color filter layers (typically red, green and blue), using these filters in conjunction with three separately tuned sets of gratings (tuned for these different colors) would permit light-field imaging in color.

It is possible to extract three-dimensional information about the source object that is generating the responses of the diodes. Light originating at any given point in space visible to the imager will generate a unique set of responses in the detectors in the imager. In particular, a point at location (x,y,z) will illuminate a point $(x_s, y_s)$ on the imager (defining the plane of the imager as $z_s=0$) with an intensity proportional to $$B_s = \frac{B}{(x-x_s)^2 + (y-y_s)^2 + z^2}$$

with incident angles:

$$\theta_x = \cos^{-1}\left(\frac{z}{\sqrt{(x-x_s)^2 + z^2}}\right)$$

$$\theta_y = \cos^{-1}\left(\frac{z}{\sqrt{(y-y_s)^2 + z^2}}\right)$$

where $\theta_x$ is the azimuth and $\theta_y$ is the altitude. The resulting illumination of individual diodes in that region will follow the equations above, such that, for example, the "zero degree, horizontal" diode will see a brightness of $$D_{0H} = \frac{I_o}{(x-x_s)^2 + (y-y_s)^2 + z^2} \cdot \frac{(1 + \cos(k\theta_x))}{2}$$

$$D_{0H} = \frac{I_o}{(x-x_s)^2 + (y-y_s)^2 + z^2} \cdot \frac{\left(1 + \cos\left(k\cos^{-1}\left(\frac{z}{\sqrt{(x-x_s)^2 + z^2}}\right)\right)\right)}{2}$$

and so on, such that any given diode's response to illumination from a given point in space can be calculated. That is, one can define a response $r(x_s, y_s, a)$ (where $x_s$ and $y_s$ are as above, and a is an index from 1 to 8 representing the phase associated with the diode) to any given stimulus $s(x,y,z)$. This can be rewritten in vector form by giving each diode an index i, (such that each combination $x_s, y_s, a$ has a unique i: for example, for an N×N array with 8 possible angles, $i = a + 8*x_s + N*8*y_s$, such that i ranges from 1 to $8N^2$). One can then define an overall response in the array r to a given stimulus point $s(x,y,z)$, where each entry in r is defined as above. If one then calculates this vector for every stimulus location in a volume with dimensions X, Y and Z, (defined as integer multiples of the resolution one wants to image the volume with), one can define a single index, j, for these points in the volume, defined similarly to above. Thus one can define any pattern of light sources in the volume of interest by a second vector s. Since light at each point in s will cause a response in each diode in r, and the effects of each of these light sources will add linearly, one can define a matrix A, where each entry a(i,j) is defined as the response of diode i to a unit light stimulus at point j. It follows that $r = As,$ where r is now a vector of diode responses that captures the total response of the array to a given stimulus pattern in three dimensions.

It is noted that A is not a square matrix, since r has a total of $8N^2$ entries, whereas s has XYZ entries. In most cases where a reasonably high resolution is called for, one can assume that roughly, X=Y=N, and Z is on the order of N as well. Thus one can typically assume that s has many more entries than r (on the order of N/8 times as many).

In order to find s (i.e., the three-dimensional structure of the object being imaged), matrix A is inverted by:

$s = A^{-1} r.$

However, such an inversion is not mathematically possible since A is not square matrix, but is "taller" than it is "wide". There will not be enough information in a planar imager to distinguish all possible structures in a volume being imaged since there are simply more unknowns (the entries in s) than there are equations to define them (the entries in r). Thus a solution to the problem requires that additional constraints be imposed. Two non-limiting examples are discussed below.

Example 1

Using Light Field Data for Refocusing and Range-Finding

One way to constrain the problem described above is to assume that s is the result of visual information at a particular focal depth, and finding the best estimate for what the image should look like if the detected light originated only in that plane. s now describes a plane with dimensions X×Y, such that s has $X*Y=N^2$ entries. Since this is now actually less than the size of r, A is still not square, but is now "wider" than it is "tall" such that the problem is now-over defined. By using a pseudo-inverse, usually defined for over constrained systems as $(A^T A)^{-1} A^T$, one can extract a best fit for s given r. If there is a reasonably good fit (as there will be if the focal plane chosen is the correct one), then this approach will yield a good approximation of the actual object scene. In particular, if the approximation of s is:

$s' = p_{inv}(A) r,$ where $p_{inv}(A)$ is the pseudo-inverse of A, and given that A was chosen such that $r = As,$ then by the definition of the pseudo-inverse, the total error $|s' - s|$ is minimized.

This approach can also be applied to data from a normal imager. However, since the mapping between s and r is different, the matrix A will be different, as will as its pseudo-inverse, $p_{inv}(A)$. In particular, the degree to which a pseudo-inverse provides a useful result depends upon the singular values of A (similar to eigenvalues in a square matrix). Moreover, the larger the singular values of a matrix, the less sensitive the inversion process is to small errors and noise. The type of array described here, when used to compute the stimulus s for a given focal plane offset from the plane of the imager, provides a significantly richer description resulting in a matrix with larger singular values. An example of this is shown in FIG. 15 for two 16×16 arrays 101a and 101b, one where each pixel simply detects light, and the other where each pixel contains two fingered diodes and a metal grating, such that sets of four pixels form a cell. For a focal plane four pixel widths from the imager plane, the grating based design generates a conversion matrix A whose singular values are consistently larger, by as much as a factor of 100 than those for a normal imager. As a result, calculating the pseudo-inverse for a grating-based imager yields a more accurate, lower noise result than with a normal imager.

A second result of this approach is that one can calculate an error term based upon using the pseudo inverse. In particular, calculating an estimate of r as:

$r' = As'$ lets one then find an error term associate with this estimate:

$err = |r' - r|.$

If the estimate s' accurately leads to the entries in r, then this error term will be small. This will be true if the source of the image was in fact at the focal depth used when estimating A. On the other hand, if the image originates at some other focal depth, then the estimate will likely be wrong, and the error term will be larger. Simulations confirm this (again for the 16×16 array), with this error term minimized when the actual focal depth is chosen. This is distinct from the case of a normal imager where this error increases monotonically with estimated focal depth regardless of reality (see FIG. 15b). Since this error term can be calculated using only A and r without knowing s a priori, it should be possible to use this error term to recognize the "correct" focal depth when refocusing the image. This information alone can be used for range-finding in a light field independent of the details of the object(s) being imaged.

The method described herein above need not be applied to the entire image, but can be applied to subsections of the image such that they can be refocused independently and/or their range found, leading to better overall focus and/or a range map across the image.

Example II

Using Light Field Data for Extraction of Sparse Fluorescent Sources

Another exemplary application pertains to imaging the three dimensional structure of fluorescing cells in tissue. Since the goal of such an application would be to be able to independently quantify the fluorescence of multiple cells at different focal planes, refocusing is not an appropriate approach. However, if one adds the two additional constraints: i) that all entries in s must be strictly positive (there is no such thing as negative fluorescence), and ii) that the fluorescent sources are relatively sparsely distributed in the volume being imaged, one may assume that the number of fluorescent cells is smaller than $N^2$, the number of pixels. If this holds true, then one can find each of these sources iteratively and in order of brightness as follows:

a) correlate r with the expected response to each possible entry in s as:

$c = rA^T;$ b) find the index, j, of s that correlates best with r (index of the maximum entry in c);
c) estimate the maximum value of s at this index that would yield a response r' such that r(i)'<r(i) for all indices i. This implies that r(i)−gA(j,i)>0, where A(i,j) is the $i^{th}$ entry of the $j^{th}$ column. Therefore g=min(r(i)/A(j,i)) across all values of i;
d) reduce by a factor λ, where 0<λ<1 and add to the existing estimate of s $s'(j) = s'(j) + \lambda g;$ e) update residual value of r:

$r = r - As';$ f) repeat steps (a-e).

Each iteration of this algorithm finds the most likely dominant point source of the light field seen in r, includes that source in the estimate of the stimulus, s', then removes that portion of the effect from r permitting the algorithm to find the next most dominant source. λ is chosen to be <1 so that no entry of r is driven to zero prematurely. In a simulation that provided reasonable results, λ=0.5.

The various embodiments described herein are compatible with a variety of integrated light detectors/sensors including, without limitation, reverse-biased p-n junction diodes, forward bias diodes (i.e., photovoltaics), p-i-n diodes, charge-coupled devices (CCDs), single-photon avalanche diodes, or pairs of interleaved N+/p-substrate diffusion diodes.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:
1. A method for extracting incident light-angle information from a light source object, comprising:
providing a two-dimensional, M×N sensor array of ASP-light-field detectors, where M, N are integers equal to or greater than one, wherein the array of ASP-light-field detectors includes:
a plurality of nano-scale to micron-scale ASPs disposed in and on a substrate, wherein each ASP comprises:
a phase grating having a period, p1, further wherein the phase grating is characterized by a periodic variation of refractive index in a direction transverse to an incident light field and forms a periodic intensity pattern in a Talbot plane below the phase grating;
an amplitude transmission analyzer grating having a period, p2 disposed in the Talbot plane; and
a sensor disposed at a selected distance below the analyzer grating;
positioning the sensor array adjacent the light source object; and determining the light source object's location in three-dimensional space based upon light from the object that is incident on the sensor array.

2. The method of claim 1, wherein the light source object comprises a plurality of fluorescent cells in a tissue.

3. The method of claim 2, further comprising detecting the location of individual fluorescent cells by triangulating back from the incident light angles detected by each sensor in the array.

4. The method of claim 2, further comprising detecting a change in the fluorescence of an individual fluorescent cell independent of another of the fluorescent cells by triangulating back from the incident light angles detected by each sensor in the array.

5. The method of claim 1, wherein each of the plurality of ASPs is a lensless ASP.

6. The method of claim 5, comprising extracting the incident light-angle information from the light source object without the use of a lens.

7. A method for determining a location of a distant object, comprising:
providing an ASP sensor array according to claim 5;
providing a lens system having a focal plane, in an object space adjacent the ASP sensor array; and
detecting one of a divergence and a convergence of light from the object that is incident on the ASP sensor array.

8. The method of claim 7, wherein the distant object comprises a plurality of light-emitting objects.

9. The method of claim 1, further comprising providing a color filter in or on the ASP sensor array.

10. The method of claim 9, wherein each ASP comprises a plurality of color filter layers.

11. The method of claim 10, wherein each ASP further comprises a respective plurality of color-tuned diffraction gratings, whereby color imaging is enabled.

* * * * *